US012805790B2

(12) United States Patent
Cotero et al.

(10) Patent No.: US 12,805,790 B2
(45) **Date of Patent: *Nov. 24, 2026**

(54) NEUROMODULATION TO TARGET GLUCOSE TRANSPORTER AND/OR INCRETIN PATHWAYS

(71) Applicant: GE Precision Healthcare LLC, Wauwatosa, WI (US)

(72) Inventors: Victoria Eugenia Cotero, Troy, NY (US); Christopher Michael Puleo, Niskayuna, NY (US); John Frederick Graf, Ballston Lake, NY (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/232,311

(22) Filed: Jun. 9, 2025

(65) Prior Publication Data

US 2025/0352127 A1 Nov. 20, 2025

Related U.S. Application Data

(63) Continuation of application No. 18/766,198, filed on Jul. 8, 2024, now Pat. No. 12,336,835, which is a (Continued)

(51) Int. Cl.

*A61B 5/00* (2006.01)
*A61B 5/145* (2006.01)

(Continued)

(52) U.S. Cl.

CPC ........ *A61B 5/4244* (2013.01); *A61B 5/14532* (2013.01); *A61B 5/4848* (2013.01);

(Continued)

(58) Field of Classification Search

CPC .............. A61N 7/00; A61N 2007/0026; A61N 2007/0021; A61N 2007/003;

(Continued)

(56) References Cited

U.S. PATENT DOCUMENTS

| | | | |
|---|---|---|---|
| 2003/0060711 A1 | 3/2003 | Michaeli | |
| 2003/0216648 A1 | 11/2003 | Lizzi et al. | |

(Continued)

FOREIGN PATENT DOCUMENTS

| | | |
|---|---|---|
| EP | 2821103 A1 | 1/2015 |
| JP | 2017051810 A | 3/2017 |

(Continued)

OTHER PUBLICATIONS

JP application 2024-166042 filed Sep. 25, 2024—Office Action issued Dec. 24, 2025; Machine Translation; 6 pages.

(Continued)

*Primary Examiner* — Gerald Johnson

(74) *Attorney, Agent, or Firm* — Fletcher Yoder P.C.

(57) ABSTRACT

The subject matter of the present disclosure generally relates to techniques for neuromodulation that include applying energy (e.g., ultrasound energy) into the tissue to cause a change in a glucose transporter pathway molecule and/or an incretin pathway molecule. In one embodiment, the neuromodulation is performed as a treatment of a metabolic disorder.

14 Claims, 18 Drawing Sheets

Related U.S. Application Data continuation of application No. 17/437,731, filed as application No. PCT/US2020/022418 on Mar. 12, 2020, now Pat. No. 12,029,577.

(60) Provisional application No. 62/826,517, filed on Mar. 29, 2019, provisional application No. 62/817,373, filed on Mar. 12, 2019.

(51) Int. Cl.

| | |
|---|---|
| ***A61N 7/00*** | (2006.01) |
| ***G01N 33/66*** | (2006.01) |
| ***G01N 33/68*** | (2006.01) |

(52) U.S. Cl.

CPC ............... *A61N 7/00* (2013.01); *G01N 33/66* (2013.01); *G01N 33/6872* (2013.01); *A61N 2007/0026* (2013.01)

(58) Field of Classification Search

CPC ............... A61N 2007/0052; A61P 1/16; A61B 2090/378; A61B 5/4244

See application file for complete search history.

(56) References Cited

U.S. PATENT DOCUMENTS

| | | | | |
|---|---|---|---|---|
| 2005/0099824 | A1 | 5/2005 | Dowling et al. | |
| 2005/0250739 | A1* | 11/2005 | Christian | C07H 5/04 536/18.7 |
| 2011/0178441 | A1* | 7/2011 | Tyler | A61N 7/00 601/2 |
| 2011/0301662 | A1 | 12/2011 | Bar-Yoseph et al. | |
| 2014/0155789 | A1* | 6/2014 | Nonogaki | A61N 7/00 601/2 |
| 2016/0128767 | A1* | 5/2016 | Azamian | A61B 18/1492 606/41 |
| 2017/0007310 | A1 | 1/2017 | Rajagopalan et al. | |
| 2017/0333122 | A1 | 11/2017 | Rajagopalan et al. | |
| 2017/0333708 | A1 | 11/2017 | Conde et al. | |
| 2019/0069949 | A1* | 3/2019 | Vrba | A61B 17/320068 |
| 2020/0215266 | A1 | 7/2020 | Koya et al. | |
| 2021/0370037 | A1* | 12/2021 | Miao | A61K 9/0009 |
| 2022/0054864 | A1 | 2/2022 | Baldoni | |

FOREIGN PATENT DOCUMENTS

| | | | | |
|---|---|---|---|---|
| WO | WO-2004021858 | A2 * | 3/2004 | A61N 1/05 |
| WO | 2014024201 | A1 | 2/2014 | |
| WO | 2018081826 | A1 | 5/2018 | |

OTHER PUBLICATIONS

JP2017-051810A English Abstract—Espacenet.com Mar. 20, 2026; 1 page.

International Search Report and Written Opinion for PCT Application No. PCT/US2020/022418, mailed Jul. 7, 2020, 11 pgs.

JP application 2021-550063 filed Aug. 26, 2021—Office Action issued Nov. 29, 2023; Machine Translation; 10 pages.

Supplementary European Search Report for EP20769481 mailed Apr. 3, 2024, 10 pages.

* cited by examiner

NEUROMODULATION TO TARGET GLUCOSE TRANSPORTER AND/OR INCRETIN PATHWAYS

CROSS-REFERENCE TO RELATED APPLICATIONS

This application is a continuation of U.S. application Ser. No. 18/766,198, entitled "NEUROMODULATION TO TARGET GLUCOSE TRANSPORTER AND/OR INCRETIN PATHWAYS," filed Jul. 8, 2024, which claims priority to U.S. application Ser. No. 17/437,731, entitled "NEUROMODULATION TO TARGET GLUCOSE TRANSPORTER AND/OR INCRETIN PATHWAYS," filed Sep. 9, 2021, which claims priority to PCT Application No. PCT/US2020/022418, entitled "NEUROMODULATION TO TARGET GLUCOSE TRANSPORTER AND/OR INCRETIN PATHWAYS," filed Mar. 12, 2020, which claims priority to and the benefit of U.S. Provisional Application No. 62/817,373, entitled "NEUROMODULATION TO TARGET GLUCOSE TRANSPORTER AND/OR INCRETIN PATHWAYS," filed on Mar. 12, 2019, and U.S. Provisional Application No. 62/826,517, entitled "NEUROMODULATION TO TARGET GLUCOSE TRANSPORTER AND/OR INCRETIN PATHWAYS," filed on Mar. 29, 2019, the contents of which are incorporated by reference in their entirety herein for all purposes.

STATEMENT REGARDING FEDERALLY SPONSORED RESEARCH & DEVELOPMENT

This invention was made with government support under contract number HR0011-18-C-0040 awarded by the Defense Advanced Research Projects Agency (DARPA). The government has certain rights in the invention.

BACKGROUND

The subject matter disclosed herein relates to neuromodulation or secretory cell modulation via stimulation of peripheral nerve or secretory cell components in target tissues and, more specifically, to techniques for targeting pathways such as the glucose transporter and/or incretin pathways via neuromodulation.

Neuromodulation or nerve stimulation involves using stimulating devices to target particular neural pathways for clinical benefit. For example, stimulation of central nervous system structures may be used to treat pain. Certain nerve stimulation strategies use permanently-implanted electrodes, transcutaneous electro-magnetic fields, or adapted brain stimulation technologies to stimulate large nerves that can be accessed by an implanted device or nerves close to the surface of the skin. However, the smaller nerves of the peripheral nervous system that reside in or terminate in organs are more difficult to target than the larger central nervous system structures. The anatomical structure of the peripheral nervous system (PNS) presents difficult challenges. Within peripheral nerves, individual axons are tightly bundled in groups (fascicles) and wrapped within protective tissue. This makes it difficult to selectively stimulate subsets of axons that terminate in specific organs and uniquely modulate the function of communicating cells within that organ. New nerve stimulation methods are needed to non-invasively stimulate specific targets and correlate organ-specific neural activity with function for broad clinical translation and treatment of clinical conditions.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
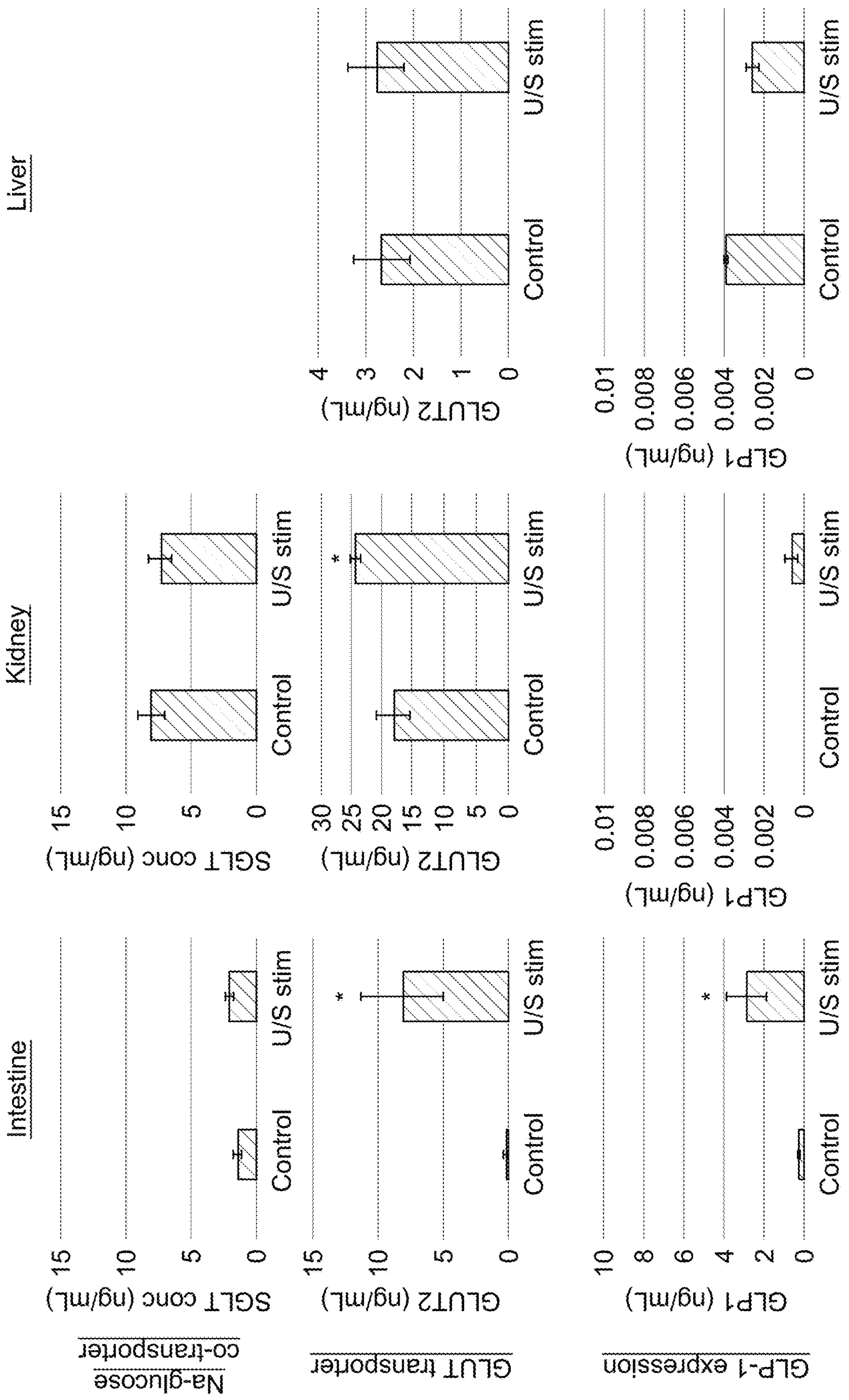
FIG. 1 shows protein concentration levels as measured by ELISA for sodium glucose co-transporter protein (SGLT1 in the intestine or SGLT2 in the kidney), glucose transporter 2 (GLUT-2), and glucagon-like peptide-1 (GLP-1) in liver, kidney, and intestinal tissues collected from both liver-stimulated and sham control Fatty Zucker animals, whereby intestinal tissue samples were collected using a lumen stripping technique to enable examination of both glucose transporter protein concentration or translocation changes across the luminal barrier tissue.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "such as," "e.g.," "including," and "in one (an) embodiment."

Metabolic pathways are controlled through complex feedback. For example, during food scarcity, the neurological endocrine system may be down-regulated to slow metabolism as well as increase reabsorption of excess glucose being removed by the kidneys. In contrast, an over-abundant supply of glucose may result in abnormal activation and control of these systems due to pathological functioning of the endocrine, peripheral and/or central nervous systems that may contribute to or even play a causal role in the development of Type 2 Diabetes Mellitus (T2DM)), obesity, or other metabolic disorders.

Certain medications or pharmaceutical treatments agonize or inhibit molecular pathways associated with both glucose transporters responsible for reabsorption or glucose uptake in both the kidney (SGLT2) and intestine (GLUT2), and incretin/hormonal pathways that potentiate insulin-stimulated glucose utilization. In the kidney, SGLT2 inhibitors (one class of T2DM drugs) are used to directly block reabsorption of glucose (in the S1 segment of the proximal tubule, or location of the SGLT2 protein). This in turn increases glucose excretion within urine, and therefore lowers blood glucose levels. In the intestine, SGLT1 activity is thought to participate in initiation of the translocation of GLUT2 from the basolateral to the apical side of enterocytes as changes in the co-transport of sodium (Na) into tissues causes depolarization, activation of L-type calcium channels, influx of Ca, and Ca dependent restructuring of the cytoskeletal structures involved with GLUT2 trafficking. After a meal, activation of this translocation enables increased glucose absorption from the apical/lumen into the enterocyte (and eventually blood). SGLT1 inhibitors (a second class of T2DM drugs) may block this enhanced glucose absorption mechanism, keeping more glucose within the intestine for secretion.

In addition, for diets based on refined flours/sugars and low-fiber, the capacity for rapid absorption in early segments of the small intestine due to either GLUT translocation or standard SGLT1 activity may inhibit food/sugars from reaching distal parts of the ileum. This is problematic in that, in this lower part of the small intestine (i.e. ileum) reside glands that secrete incretins, such as GLP1, a class of hormones involved in metabolism. Signaling from these hormones may signal other peripheral tissues to modulate their response to insulin (i.e. insulin sensitivity). GLP agonists, another class of T2DM drug, acts to mimic the incretin and functions such as activation insulin secretion and sensitization. The activity of SGLT1 and SGLT2 may be affected by adrenergic signaling through coupling to adrenergic receptor via adenylyl cyclase.

Provided herein are techniques for neuromodulation and secretory cell modulation that target certain metabolic pathways and molecules. Such metabolic pathways or molecules may include glucose absorption vs. excretion within the intestine (SGLT1), glucose absorption vs. excretion within the kidneys (SGLT2), and GLP/incretin signaling (modified intestinal glucose concentrations via SGLT1/GLUT2 activity and trafficking) through nerve pathways. Accordingly, in one embodiment, ultrasound energy may be applied to focus on a region of interest in metabolic tissue (liver, GI tract, pancreas, kidney). The region of interest or regions of interest may be subjected to a treatment that includes one or more doses of ultrasound energy applied once or in separate doses administered within a period of time as part of a treatment regimen. As a result of the treatment, the activity, concentration, and/or location of certain molecules of interest are changed. The changes may be present in the tissue in which the region/s of interest is located or in other tissues that are responsive to nerve signaling resulting from the direct application of energy to the region of interest. In one embodiment, the treatment is used to treat a subject having a metabolic disorder or clinical condition. In one embodiment, a patient having a metabolic disorder is treated by applying ultrasound energy to an internal tissue of the patient, wherein the ultrasound energy is applied by an extracorporeal energy application device, and wherein applying the ultrasound energy causes a change to a glucose transporter pathway molecule and/or an incretin pathway molecule in the patient. In another embodiment, a system for treating a metabolic disorder may include an energy application device configured to apply energy to an internal tissue of the subject and a controller adapted to control the energy application device to apply the energy to cause a change to a glucose transporter pathway molecule and/or an incretin pathway molecule in the subject. In one embodiment, the treatment is assessed by measuring the changes directly or measuring characteristics or indications of the changes.

Experimental results show that daily stimulation of a metabolic tissue at levels commensurate with activation of metabolic components of the autonomic nervous system serves to modify the concentration, location, and/or activity of glucose transporter pathway and or incretin pathway molecules, changing glucose uptake versus excretion levels in a therapeutic manner. In addition, this is accomplished in a local manner, not affecting other pathways that are associated with side effects. Accordingly, the neuromodulation techniques as disclosed may have fewer side effects relative to drug treatments to accomplish similar physiological changes/therapeutic outcomes and may serve as replacements or supplements to existing drug therapies for subjects with metabolic disorders.

FIG. 1 shows protein concentration as measured by enzyme-linked immune assay (ELISA) in kidney, intestine, and liver tissues in a Fatty Zucker rat diabetes model for a liver-stimulated group relative to a sham control. In the stimulated group, animals were stimulated with daily ultrasound stimulation to the liver, with sufficient power to enable activation of nerve pathways and sensory or secretory cells and provide a measured alteration of glucose transport and incretin activity, concentration, or location in downstream target tissue including intestines and kidney. Sham controls were performed by placing the ultrasound transducer on the targeted organ, but not applying the ultrasound stimulus. After the daily treatment for a period of several days, tissue samples were collected after animal sacrifice. Protein levels in the intestine (versus other tissue and/or mRNA data from the intestine) are from samples taken from scraping from the intestinal lining (thus, collecting only the apical or luminal side of the epithelial lining).

Neuromodulation of the liver results in changes in metabolic pathways and signaling molecules in both circulating markers and in other tissues. In the ultrasound-stimulated group, there was a measured decrease in circulating blood glucose associated with modification of the absorption/secretion pathways. Application of daily energy to the liver also resulted in changes in GLUT2 in the kidney and intestine and in GLP-1 in the intestine relative to the sham control.

Figure 2:
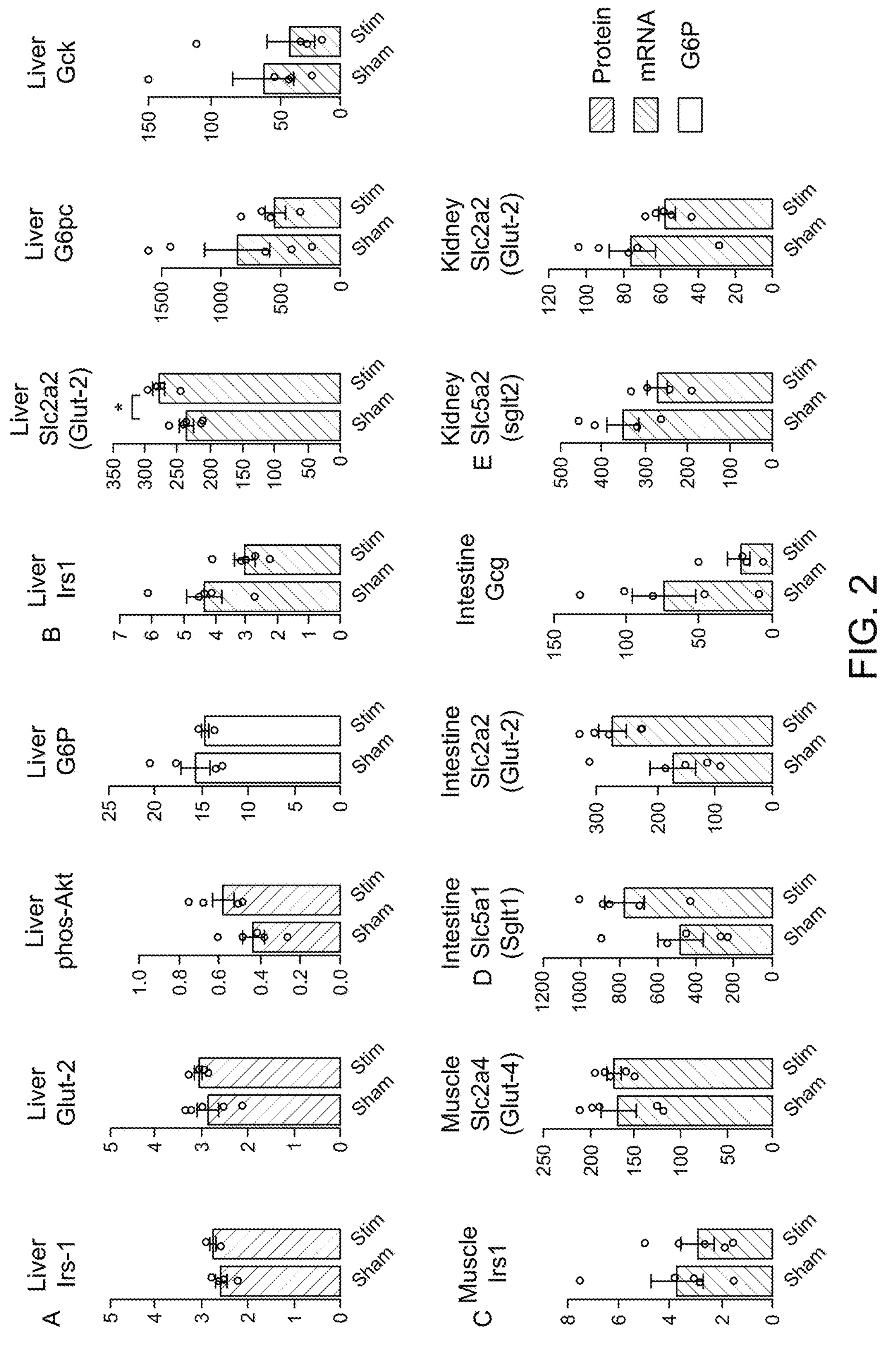
FIG. 2 shows mRNA, protein, and glucose 6 phosphate concentration levels from liver, muscle, intestine, and kidney tissues collected from both liver-stimulated and sham control Fatty Zucker animals.
Figure 3:
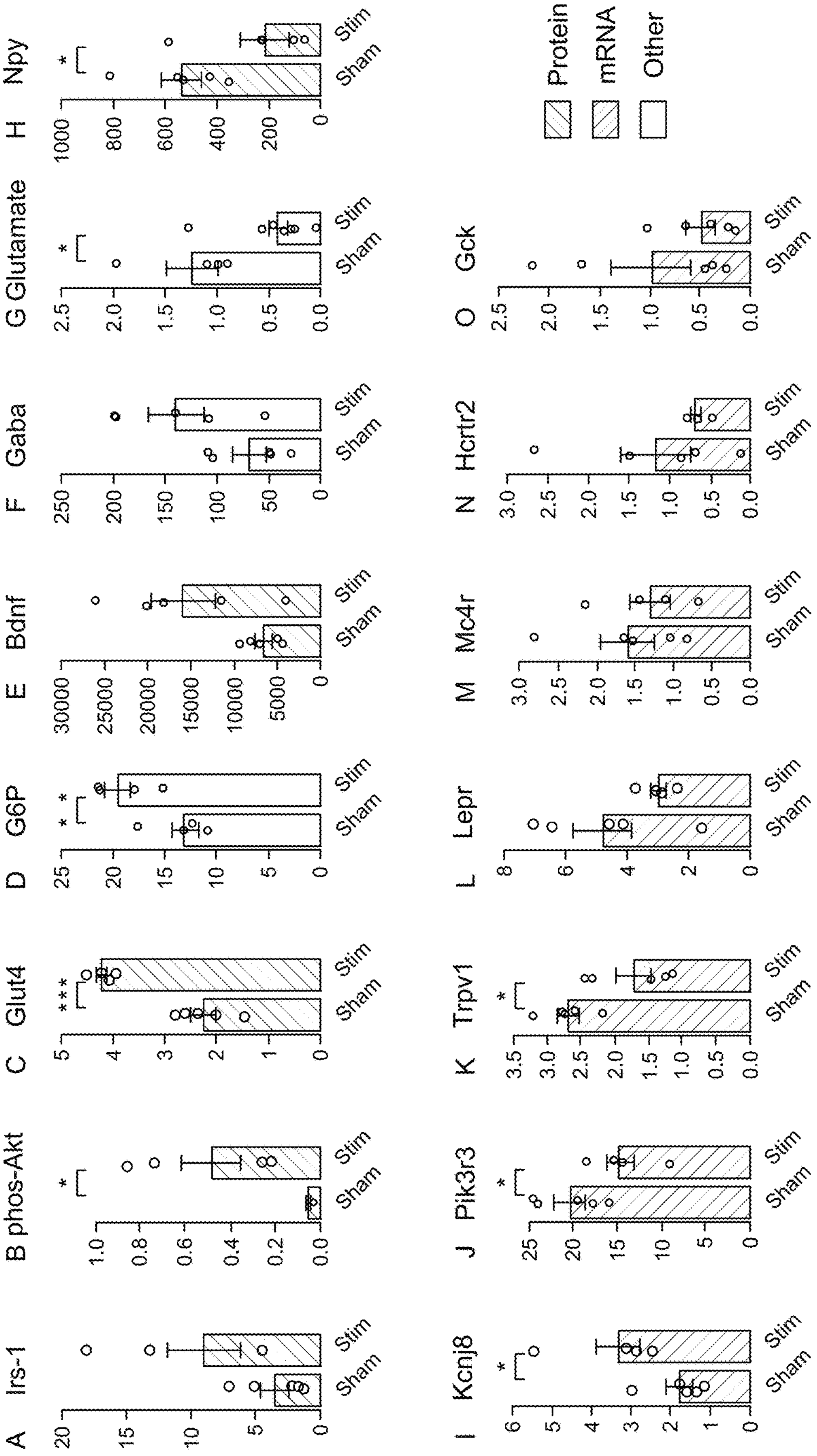
FIG. 3 shows mRNA, protein, and glucose 6 phosphate concentration levels from hypothalamus tissue collected from both liver-stimulated and sham control Fatty Zucker animals.

The changes in measured protein were accompanied by changes in RNA expression as measured by mRNA sequencing. FIG. 2 shows protein, mRNA, and assay data for various molecules of interest in liver, muscle, intestine, and kidney tissues from both liver stimulated and sham control Fatty Zucker animals treated as described in FIG. 1. FIG. 3 shows protein, mRNA, and assay data for various molecules of interest in hypothalamic tissue from both stimulated and sham control Fatty Zucker animals treated as described in FIG. 1. While SGLT2 is the important protein for glucose reabsorption, GLUT2 in the kidney is the primary means of glucose removal or excretion into the urine. Daily ultrasound stimulation in the rat model resulted in an up-regulation of both the SGLT1 and GLUT2 mRNA in the intestines but a down-regulation of both the SGLT2 and GLUT2 mRNA in the kidney. As discussed above, expression and/or translocation of the glucose transporter results in modification in glucose reabsorption versus excretion. The stimulus and resulting effects also modulates the concentration of GLP/incretins within the metabolic system. Daily ultrasound stimulation in the rat model resulted an up-regulation of both GLUT2 mRNA in the liver.

Figure 4:
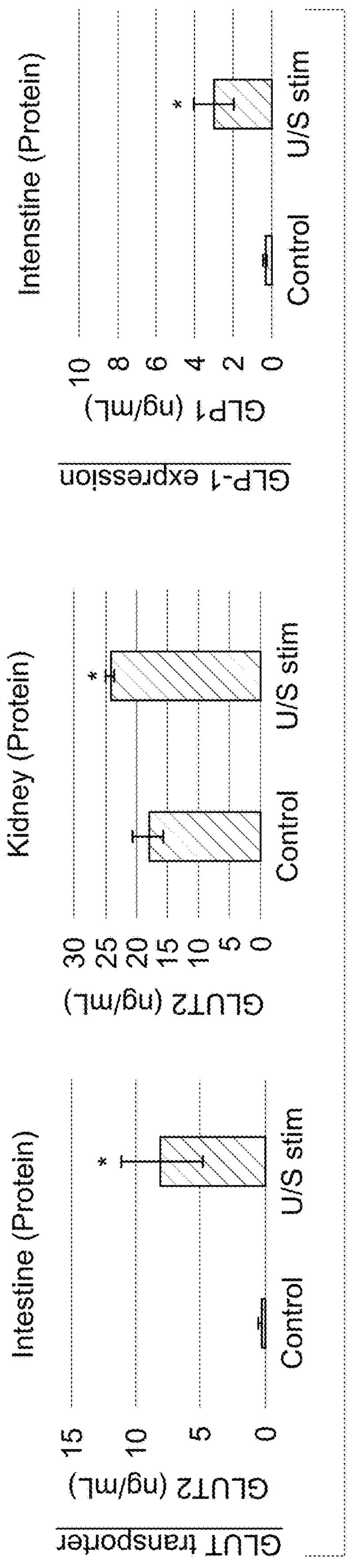
FIG. 4 shows protein concentration levels as measured by ELISA from intestine or kidney tissue collected from both liver-stimulated and sham control Fatty Zucker animals showing an increase in GLUT2 in the intestine and kidney and an increase in GLP1 in the intestine.

FIG. 4 shows protein concentration levels as measured by ELISA from intestine or kidney tissue collected from both liver-stimulated and sham control Fatty Zucker animals showing an increase in GLUT2 in the intestine and kidney and an increase in GLP1 in the intestine.

Figure 5:
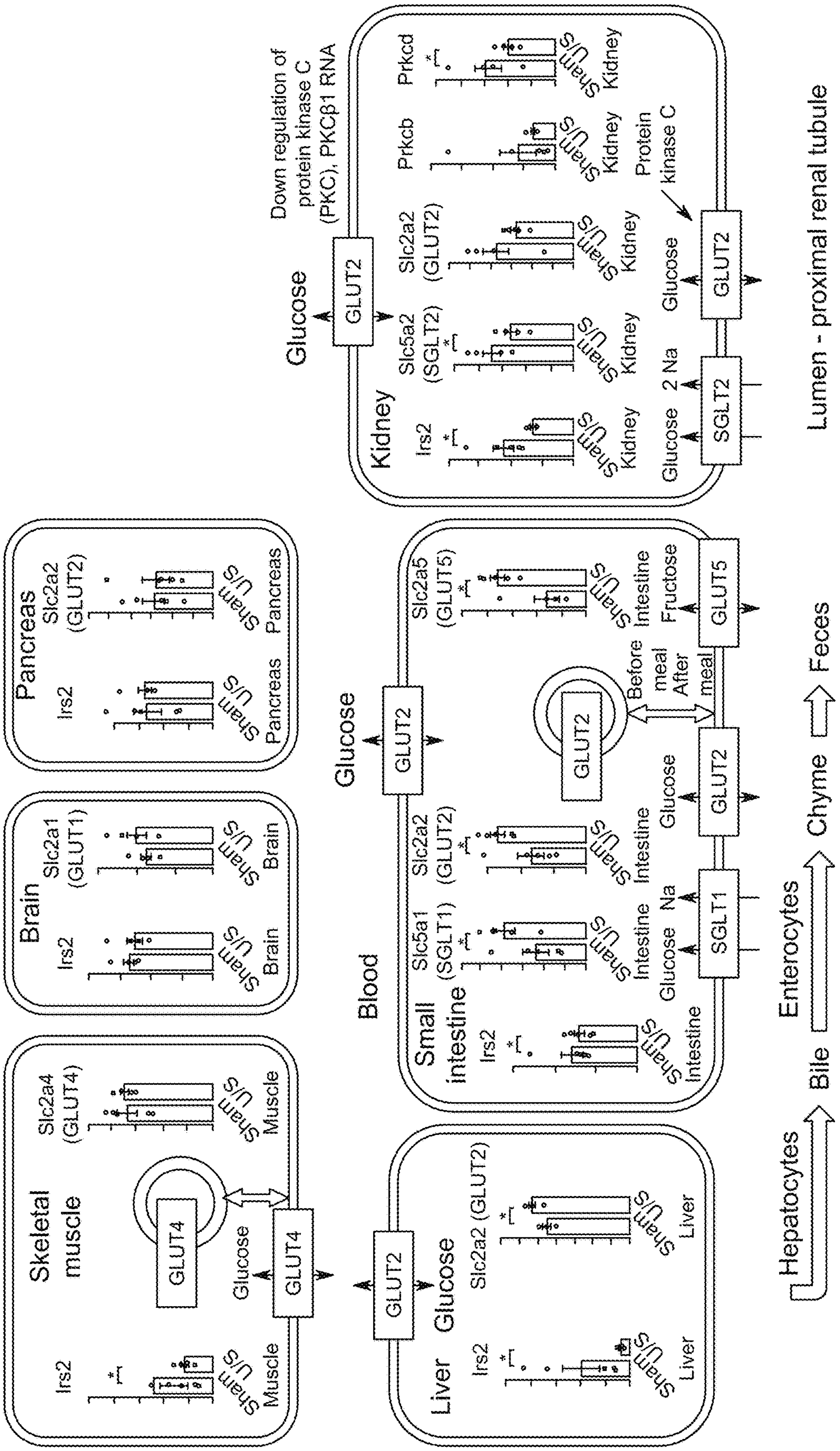
FIG. 5 shows mRNA concentration levels in various tissues collected from both liver-stimulated and sham control Fatty Zucker animals showing concurrent and interconnected changes mediated by various glucose utilization, insulin utilization, and/or metabolic associated proteins.

FIG. 5 shows mRNA concentration levels in various tissues collected from both liver-stimulated and sham control Fatty Zucker animals showing concurrent and interconnected changes mediated by cell membrane proteins. For example, glucose regulation in the liver is mediated by GLUT2, which increases as a result of daily hepatic ultrasound stimulation in the rat model. Skeletal muscle transport of glucose is mediated by GLUT4. In the kidney, a host of concurrent changes associated with daily hepatic ultrasound stimulation in the rat model. Down regulation of protein kinase C (PKC), SGLT2, GLUT2, and Irs2 may be associated with the excretion of glucose in the urine and the prevention of reabsorption in the circulation.

Figure 6:
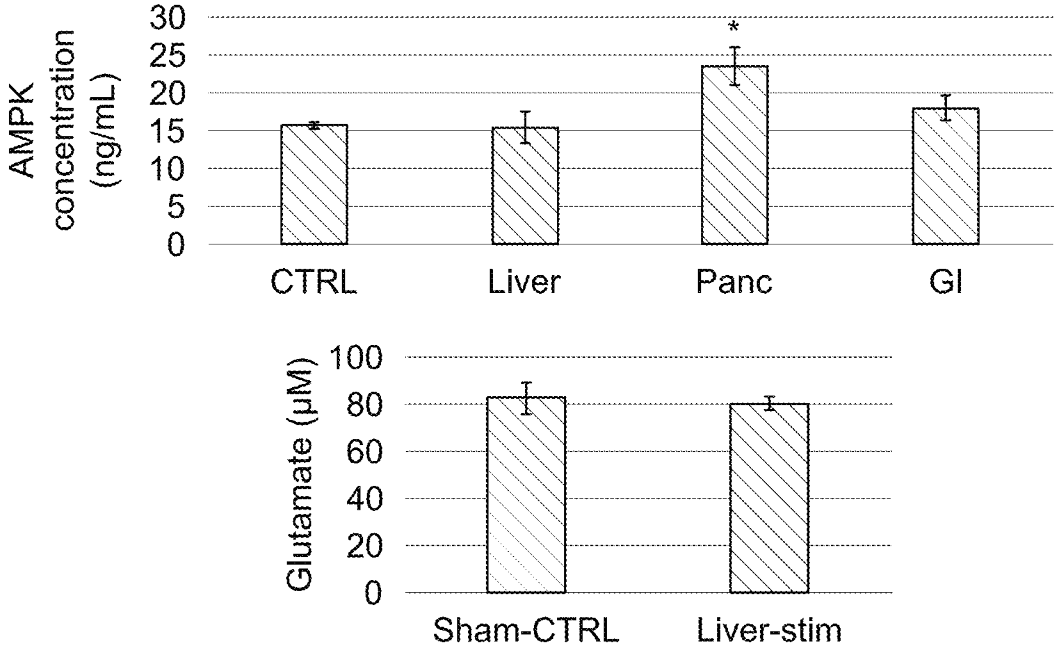
FIG. 6 shows 5' AMP-activated protein kinase concentration levels as a result of liver, pancreatic, or gastrointestinal tissue stimulation vs. control and glutamate levels as a result of liver stimulation vs. control in LPS-induced hyperglycemia model animals, showing that pancreatic stimulation is itself causing insulin release and direct insulin signaling in the hypothalamus.

FIG. 6 shows 5' AMP-activated protein kinase concentration levels as a result of liver, pancreatic, or gastrointestinal tissue stimulation vs. control and glutamate levels as a result of liver stimulation vs. control in LPS-induced hyperglycemia model animals. 5' AMP is a known measure of direct insulin signaling to the hypothalamus and activation of insulin dependent pathways.

Also provided herein are experimental results confirming direct peripheral focused ultrasound (pFUS) nerve activation by applying ultrasound stimuli to an in vitro three-dimensional (3D) nerve culture. The disclosed novel 3D culture system (FIG. 7A) provides an in vitro experimental platform for peripheral nerve investigation compared to traditional excised nerve bundle preparations. Formation of complex neural networks was observed within culture platform, and the in vitro system was used to couple ultrasound transducers and an observational fluorescence microscope to the neurons. Use of calcium indicator dyes permitted direct observation of neuron activity. Ultrasound pressures associated with in vivo neuromodulation were confirmed cause direct nerve activation in the culture system. The results demonstrated that ultrasound stimuli are capable of activating peripheral neurons.

Figure 7A:
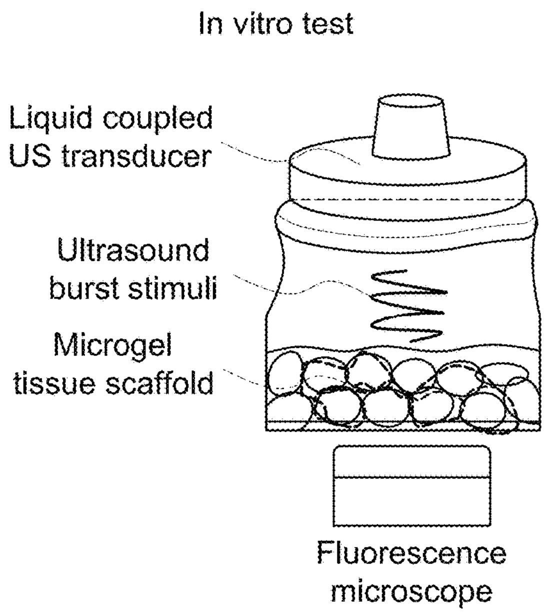
FIG. 7A shows an experimental platform for peripheral focused ultrasound (pFUS) nerve activation in an in vitro three-dimensional (3D) nerve culture.

FIG. 7A is schematic illustration of the 3D in vitro peripheral neuron culture system. Isolated peripheral neurons (i.e. dorsal root ganglion cells), DRGs) were mixed with hydrogel microparticles and co-injected into a culture plate. After injection, the microparticle hydrogels were annealed, leaving a nerve cell-laden heterogeneous scaffold that provided both a mechanically stiff growth surface for nerve cell adhesion and interconnected micropores for neurite outgrowth. DRG neurons were cultured in 200 μL of NbActiv4 with 25 ng/ml NGF in the incubator with 37° C. and 5% CO2 concentration, and 50% of Culture media was changed every 3 days. DRG neurons were incubated with Fluo-4 Direct calcium assay kit with 250×10−3 M stock solution of probenecid for Ca imaging. Briefly, 5 mL of calcium assay buffer was mixed and vortexed with 100 μL of probenecid stock solution to create a 2× loading dye solution. The dye solution was then added to the cells with media in a 1:1 ratio and incubated for 1 h before imaging to allow sufficient diffusion through the hydrogels.

Figure 7B:
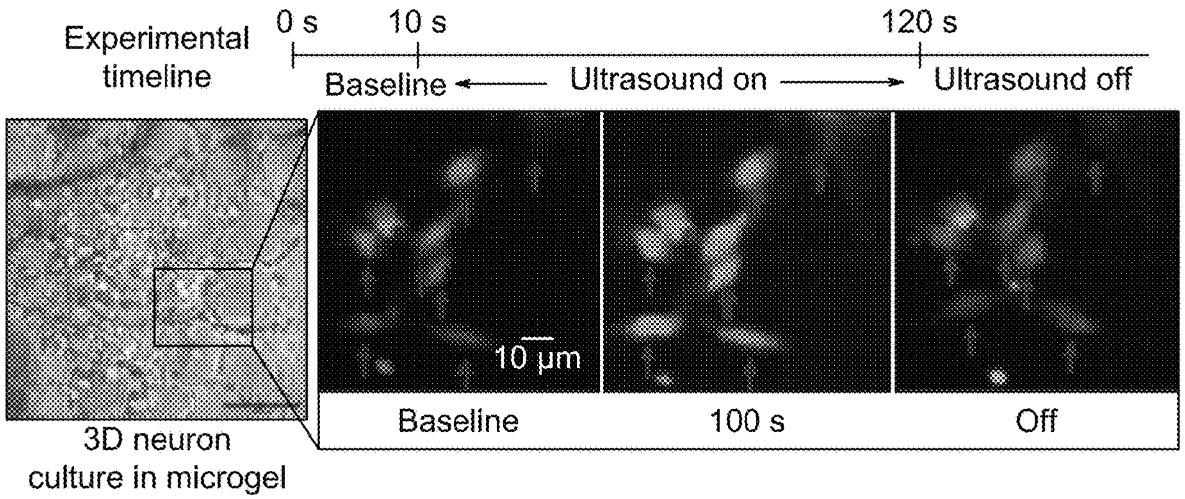
FIG. 7B shows an experimental timeline and imaged peripheral neuron networks showing transient calcium within regions-of-interest of cells in the in vitro culture of FIG. 7A.

FIG. 7B shows an experimental timeline shown along with corresponding right field and fluorescence images of DRG neuron cells in 3D hydrogel scaffold. Diameter of hydrogel was around 100 μm, and the pore size of hydrogel particles was around 1 μm. DRG neuron cells grew between pores of hydrogel particles three dimensionally. The fluorescence images show a time lapse of calcium imaging during pFUS stimulation. pFUS stimulation was on at 10 sec from starting point of observation and turned off again at 120 seconds after start. Ultrasound was then turned off for 2 minutes (allowing post-ultrasound or off images to be taken) prior to re-started the stimulus. Calcium concentrations of DRG neuron cells were increased after ultrasound firing as noted by an increase in fluorescence within the imaged neurons. After pFUS simulation, calcium concentration of cells returned to the same level as before stimulation.

Figure 7C:
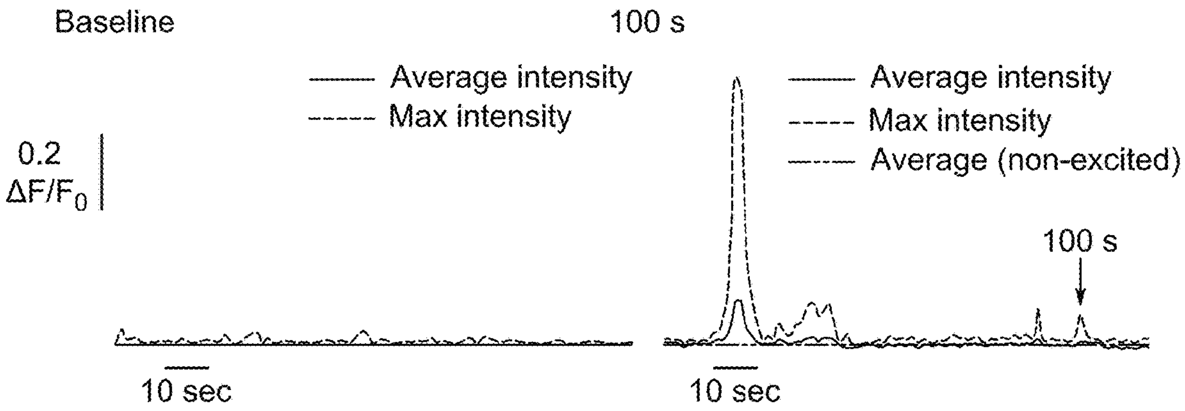
FIG. 7C shows fluorescence intensity after pulsed ultrasound stimulation of cells in the in vitro culture of FIG. 7A.
Figure 7D:
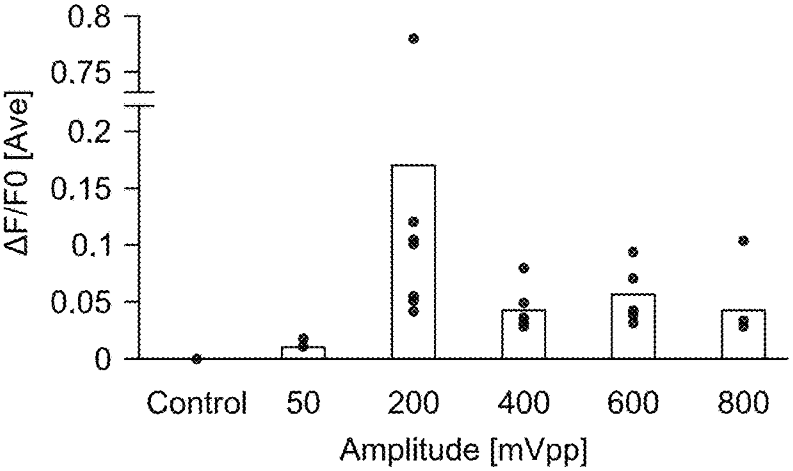
FIG. 7D shows the relationship between transient calcium and applied ultrasound pressure in the in vitro culture of FIG. 7A.

FIG. 7C shows average ΔF/F0 value and maximum ΔF/F0 value in each time points for the imaged neurons. ΔF/F0 is unchanged without pFUS stimulation (left side). On the other hand, ΔF/F0 is increased during pFUS stimulation (right side). FIG. 7D shows the relationship between different amplitude of pFUS utilized in repeat experiments, and 200 mVpp (or 0.83 MPa peak-positive pressure) showed the larger change in fluorescence within the same DRG culture (N>5 for each group). This corresponds to demonstrated effective ultrasound pressure for neuromodulation.

DRGs responded well to the 3D culture environment, adhering to the hydrogel microparticle surfaces and projecting neurites into the micropores. Both somal and synaptic nerve features were apparent in the culture, in additional to axonal projections (FIG. 7B). Axonal outgrowth resulted in neuron network formation across the micropore gaps formed between the microparticles. By imaging the peripheral neuron networks in media-loaded with Ca2+ indicator (Fluo-4 Direct calcium assay kit) calcium transient within regions-of-interest within the culture was imaged (FIG. 7B). To measure ultrasound-induced changes in calcium signaling (i.e. ultrasound-induced increased in neural activity), the ultrasound transducer (and focal point) was aligned to the center of the optical field of view (FOV). FIG. 7B demonstrate that fluorescence intensity (and thus average calcium concentrations within neurons) across the FOV increased after pulsed ultrasound stimulation (using 1.1 MHz, 136.36 μs pulse length, 0.5 ms pulse repetition period US pulses). The appearance and amplitude of these calcium transients were ultrasound pressure dependent, and the pressure applied that achieved maximum nerve activation (FIG. 7D; 0.83 MPa or 23 mW/cm$^2$ matched) corresponded to effective ultrasound pressure for neuromodulation in animal models.

In addition, provided herein is pFUS stimulation of alternative sites known to contain peripheral nerve soma and synapses, including sensory ganglion (i.e. inferior ganglion of the vagus nerve or no dose ganglion) and peripheral ganglion of mixed (sensory and efferent) innervation (i.e. sacral ganglion). Activation of the cholinergic anti-inflammatory pathway (i.e. modulation in LPS-induced circulating cytokine concentrations) was observed after ultrasound stimulation at each site (i.e. end-organ/spleen, no dose, and sacral ganglia) and showed that both the magnitude of cytokine reduction and presence of other off-target effects (i.e. simultaneous changes in blood glucose levels) were stimulation-site dependent. Lastly, intervention in a specific pathological state (i.e. reduction of LPS-induced hyperglycemia) was achieved through stimulation of multiple strategic anatomical locations associated with metabolic control. These exploratory stimulation sites included the hepatic site containing peripheral glucose sensors, the pancreas associated with insulin secreting beta cells, and an intestinal site containing incretin secreting enteroendocrine cells. Ultrasound-induced attenuation of hyperglycemia was achieved by stimulation at each of the anatomical targets. However, the magnitude of blood glucose reduction is stimulation site dependent, and the effect may be driven by different molecular mechanisms at each site. Together this data demonstrates that ultrasound stimuli are capable of direct peripheral nerve (and other neuroendocrine cell) activation, and that pFUS is capable of efficient assessment of the effectiveness of alternative therapeutic bioelectronic medicine stimulation sites.

Figure 8A:
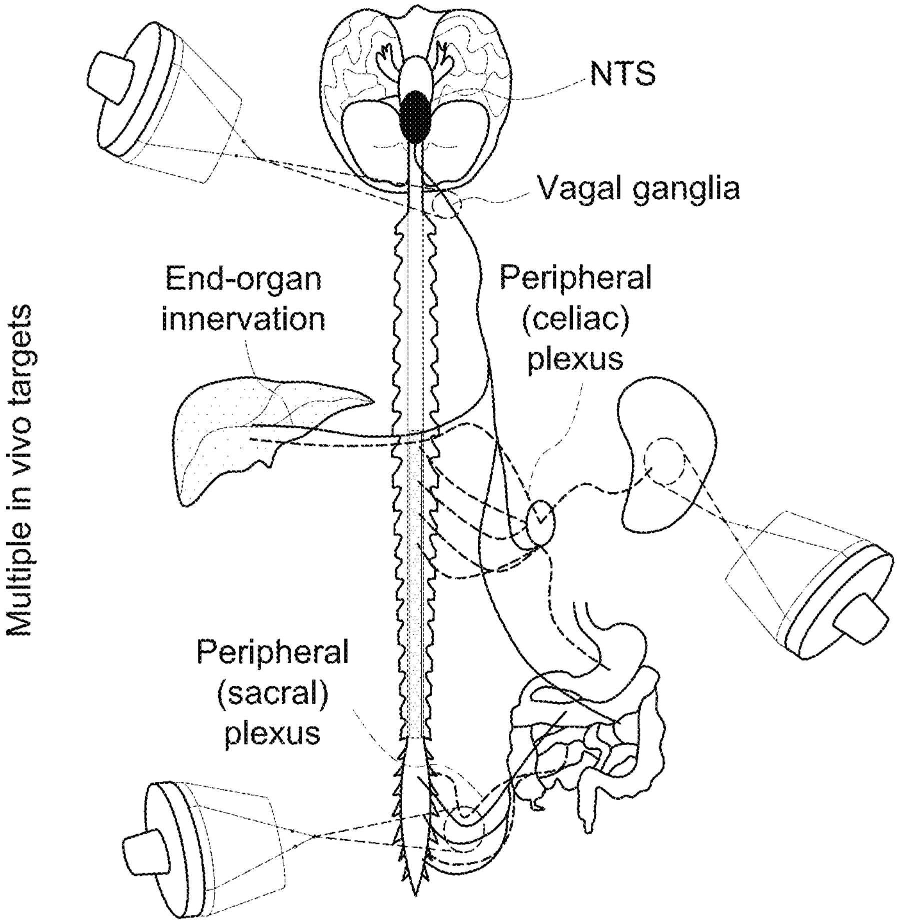
FIG. 8A shows a schematic diagram of peripheral focused ultrasound targets in which ultrasound stimuli were focused at multiple locations that contain somal and/or synaptic junctions along the vagal and parasympathetic systems.
Figure 8B:
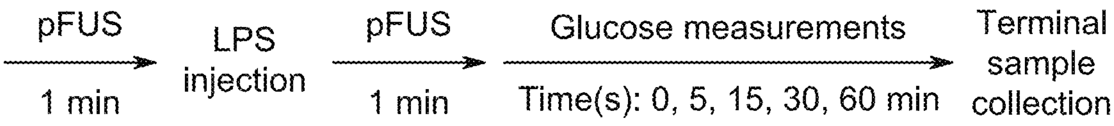
FIG. 8B shows a timeline of the ultrasound stimulation and blood sampling performed within the LPS-induced inflammation and hyperglycemia model animals.
Figure 8C:
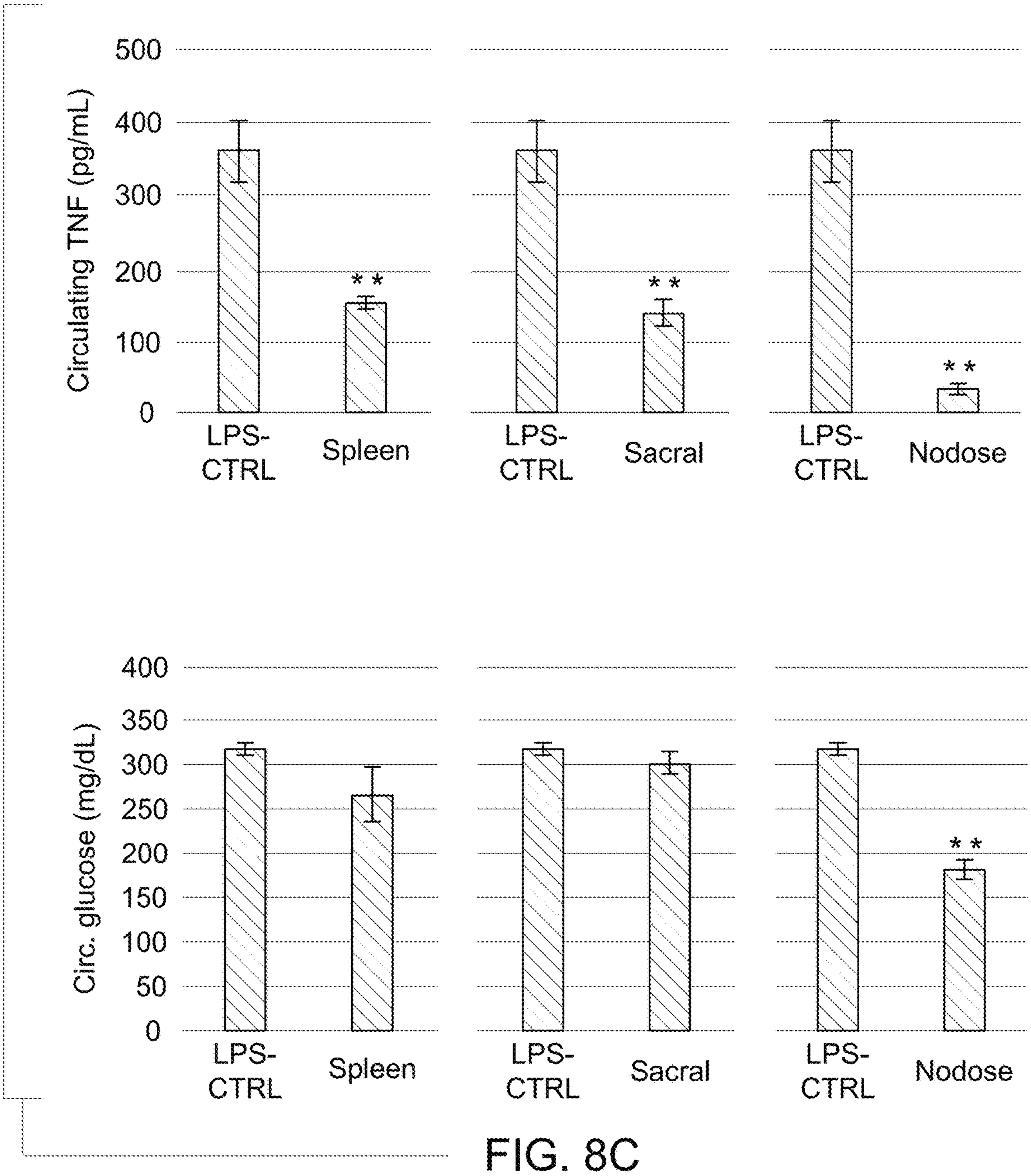
FIG. 8C shows TNF (cytokine) and glucose concentrations after pFUS targeted to different anatomical sites within the splenic and enteric cholinergic anti-inflammatory pathway (i.e. spleen, sacral ganglion, and no dose ganglion), compared to LPS alone (i.e. no ultrasound) controls.

FIGS. 8A-C show results of pFUS to activate the cholinergic anti-inflammatory pathway (CAP) at multiple locations within the brain-spleen neural pathway. FIG. 8A shows a schematic of activation, in which pFUS stimuli were focused at multiple locations that contain somal and/or synaptic junctions along the vagal and parasympathetic systems. These include the no dose ganglion (i.e. location of the soma of a majority of the vagal afferents that project into the brain), the sacral ganglion (i.e. location of mixed sympathetic and parasympathetic soma and synaptic junctions), and the spleen (i.e. locations of CAP specific neurons).

FIG. 8B depicts the timeline of in vivo neuromodulation studies performed herein, in which LPS was first introduced (as generally disclosed herein) to produce an inflammatory and hyperglycemic state. Ultrasound was then applied, and the effect of ultrasound neuromodulation was measured by comparing inflammatory or metabolic markers in the LPS control (i.e. no ultrasound stimulation) versus LPS+ultrasound stimulation cohorts.

FIG. 8C shows that splenic neuromodulation and activation of CAP is sufficient to attenuate the LPS response. In addition, the local activation of CAP at the splenic site limits additional (non-CAP or non-target) effects that are typically observed using implant-based VNS CAP activation, such as suppression of LPS-induced hyperglycemia. pFUS stimulation at both the no dose and sacral ganglion also resulted in attenuated LPS response. In addition, no dose ultrasound neuromodulation attenuated the effects of LPS to a larger extent than stimulation at either the sacral or splenic sites. This confirmed the importance of vagal afferents in triggering activation of CAP (i.e. neurons entering the CNS through the no dose ganglion), but also expands the efferent arc of the pathway to include additional vagal and sympathetic neurons.

Figure 8D:
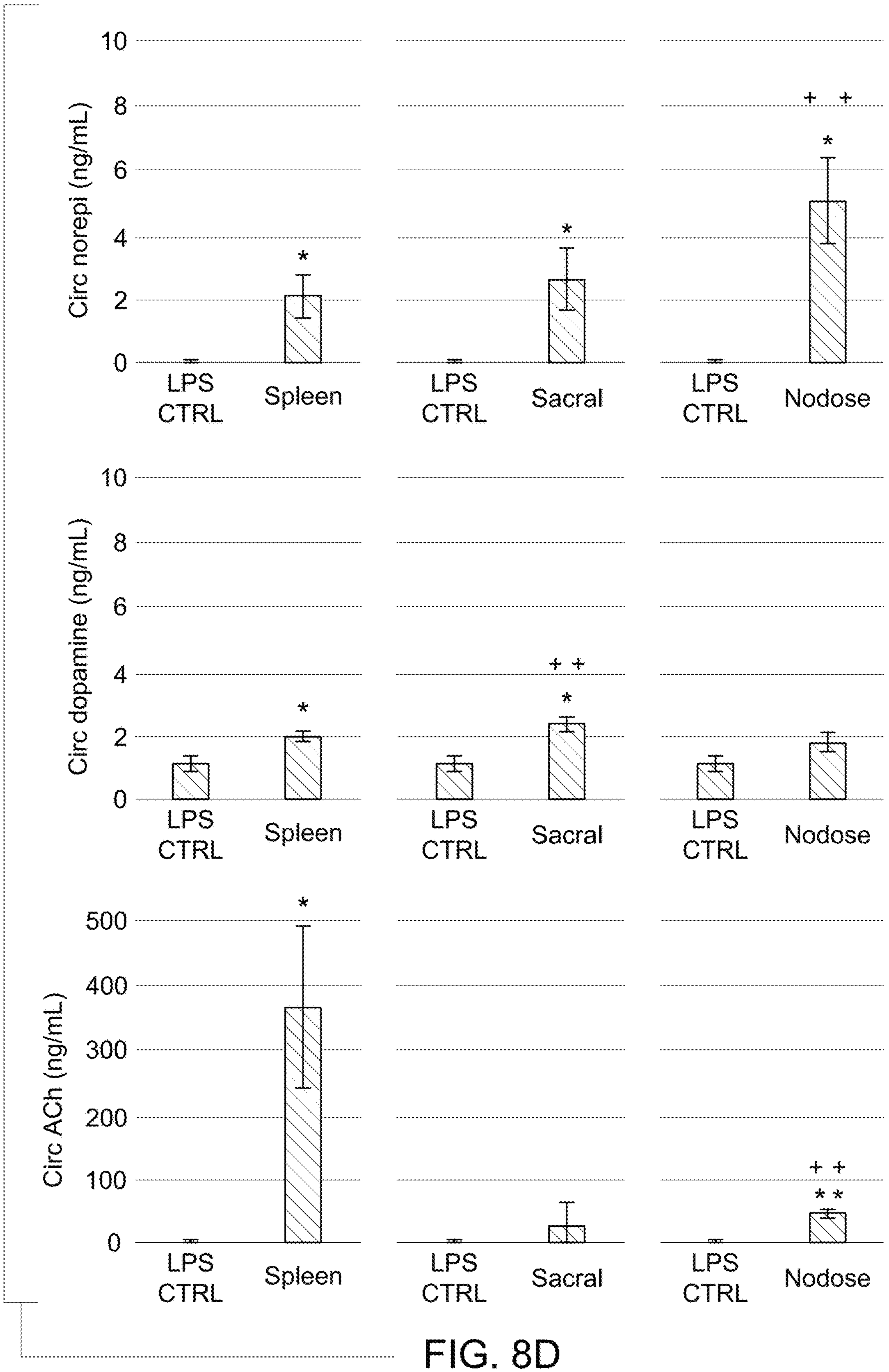
FIG. 8D shows measures of circulating/blood concentrations of neurotransmitters (i.e. epinephrine, norepinephrine, dopamine, and acetylcholine) after pFUS at the three different anatomical target sites, compared to LPS controls (LPS CTRL).

However, despite the increased level of cytokine suppression, stimulation at the no dose ganglion also resulted in suppression of LPS-induced hyperglycemia (FIG. 8D). Targeted or precision ultrasound neuromodulation at the splenic site (reported to contain no vagal afferent neurons) results in separable activation of the CAP versus other non-target pathways (such as the glucose sensing cells in the liver). Herein, separable modulation of inflammatory versus metabolic pathways is also possible at the sacral stimulation site; however, stimulation of vagal afferents at the no dose ganglion results in activation of multiple pathways (similar to traditional cervical VNS).

In addition, analysis of the change in circulating neurotransmitters after stimulation across the different sites also agrees with an updated systemic view of the CAP pathways. FIG. 8D shows measures of circulating/blood concentrations of neurotransmitters (i.e. epinephrine, norepinephrine, dopamine, and acetylcholine) after pFUS at the three different anatomical target sites, compared to LPS controls (LPS CTRL). The asterisks mark statistical significance using two-sided t-test versus LPS only control (with p-value thresholds of <0.05); double cross marks significance to both the LPS controls and alternative stimulation site data. N=5 for each experimental condition. The blood neurotransmitter profile is dominated by acetylcholine (Ach) after targeted stimulation of the splenic site, in agreement with the activation of the abundance of resident choline acetyltransferase (ChaT) positive T cells. This is accompanied by a moderate increase in catecholamines (compared to no dose stimulation) at the splenic site for activation of the ChaT T cells. In contrast, no dose stimulation resulted in a more moderate increase in Ach, but a larger increase in circulating catecholamines (in agreement with a system-wide activation of multiple efferent CAP arms, i.e. splenic and enteric CAP pathways). Finally, the sacral ganglion stimulation resulted in moderate increases in both Ach and catecholamines (compared to the splenic or no dose stimulation sites, respectively); however, stimulation at this site led to the greatest increase in circulating dopamine, suggesting activation of additional vagal-mediated anti-inflammatory pathways that have been mapped to the adrenal gland. Taken together these results demonstrated that image/anatomical targeted pFUS is capable of activating neurons at multiple locations within mapped reflexes, and may be used to assess the level of activation of target versus non-target nerve pathways within the PNS.

Figure 9A:
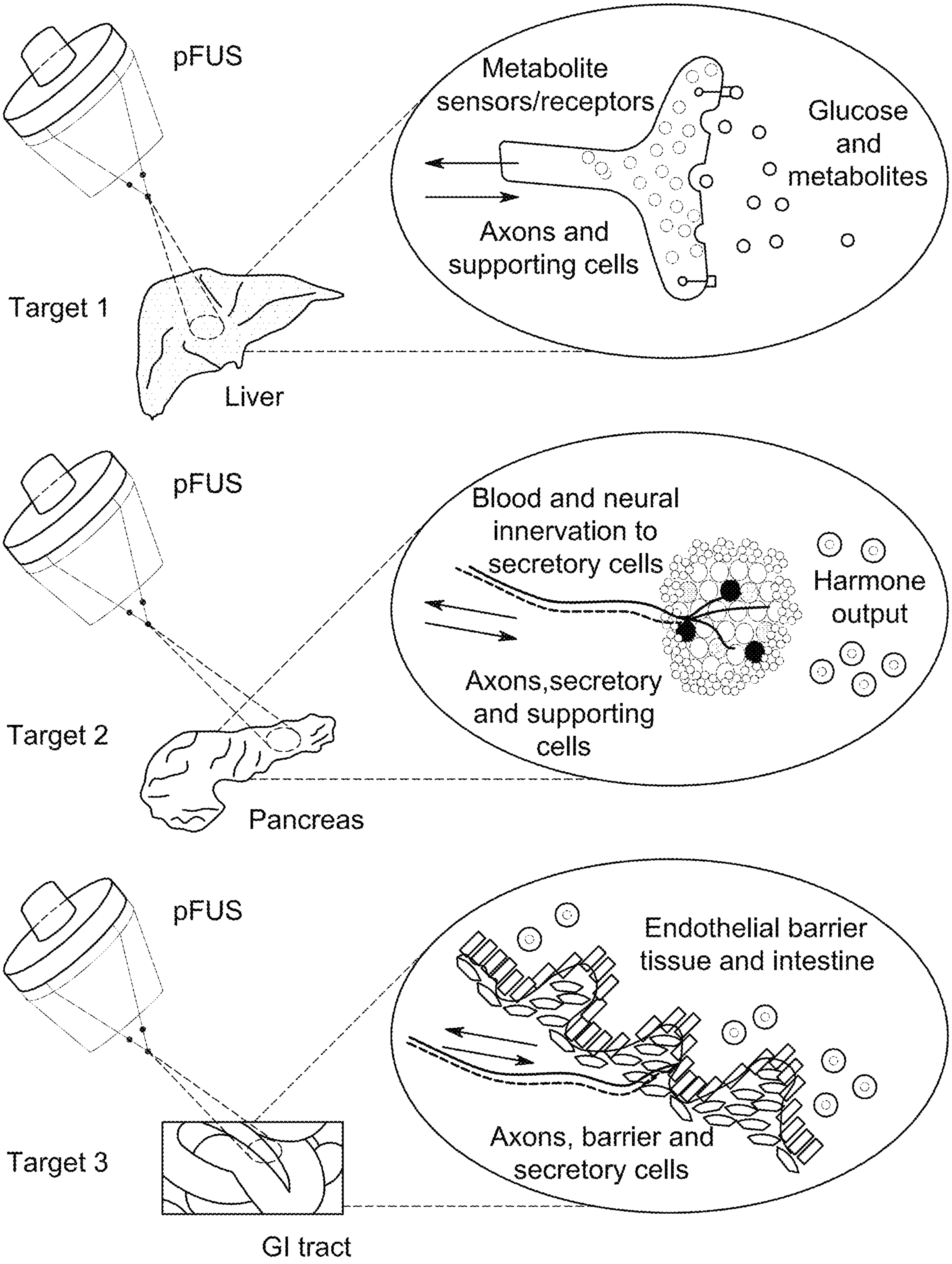
FIG. 9A is a schematic of pFUS-based precision organ-based neuromodulation in which the innervation points of known axonal populations are targeted for stimulation using focused pulsed ultrasound.
Figure 9B:
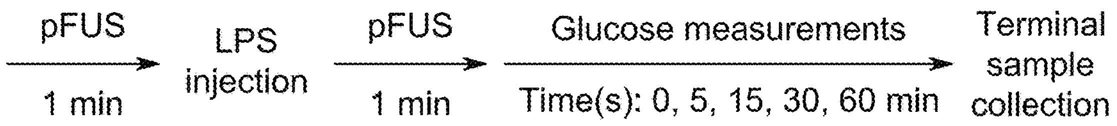
FIG. 9B is a timeline of the pFUS stimulation and blood sampling performed within the LPS-induced hyperglycemia model.
Figure 9C:
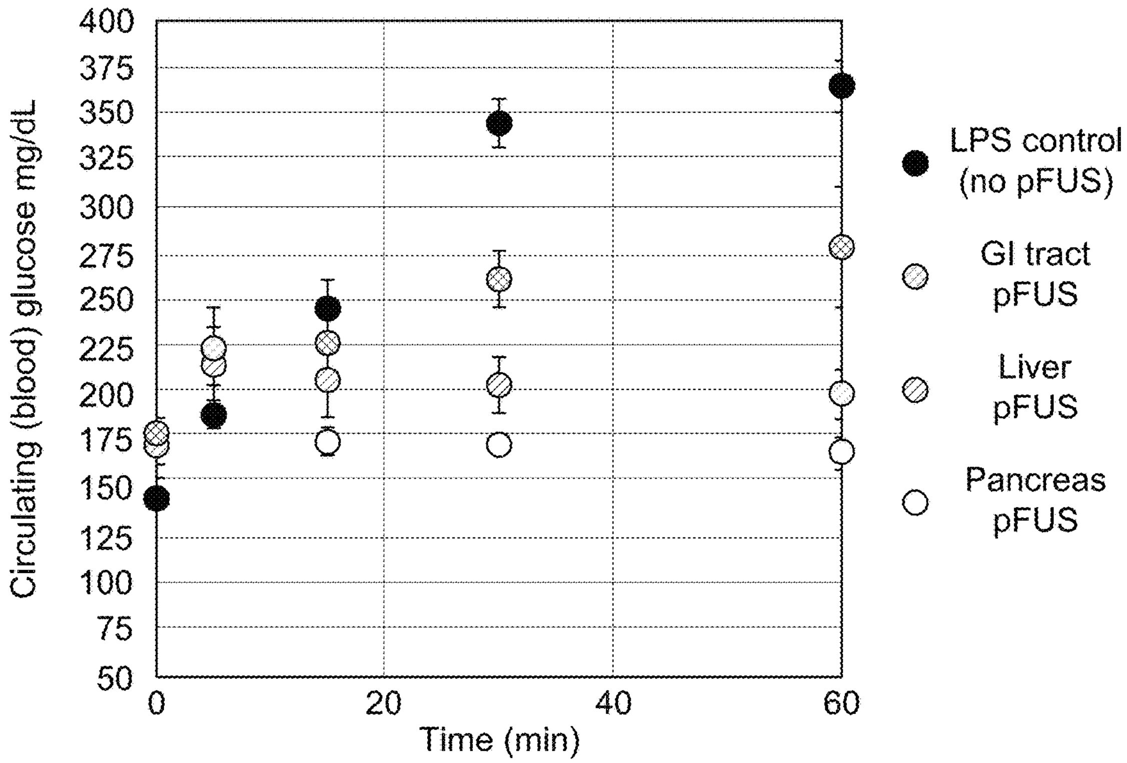
FIG. 9C shows circulating blood glucose concentrations are shown at the 0, 5, 15, 30, and 60-minute timepoints for the LPS control (no pFUS; yellow circles), hepatic pFUS (blue circles), pancreatic pFUS (purple circles), and GI pFUS (orange circles) groups.

FIG. 9A-C show organ-based peripheral focused ultrasound neuromodulation (pFUS) across the metabolic system. FIG. 9A is a schematic of pFUS-based precision organ-based neuromodulation in which the innervation points of known axonal populations are targeted for stimulation using focused pulsed ultrasound. Targets investigated herein include innervation points and sensory terminals within the liver, the pancreatic tail, and the jejunum area of the small intestine (methods used to locate and target these sites are described in the methods section). FIG. 9B is a timeline of the pFUS stimulation and blood sampling performed within the LPS-induced hyperglycemia model. FIG. 9C shows circulating blood glucose concentrations are shown at the 0, 5, 15, 30, and 60-minute timepoints for the LPS control (no pFUS; yellow circles), hepatic pFUS (blue circles), pancreatic pFUS (purple circles), and GI pFUS (orange circles) groups. n=6 for each group.

Figure 10A:
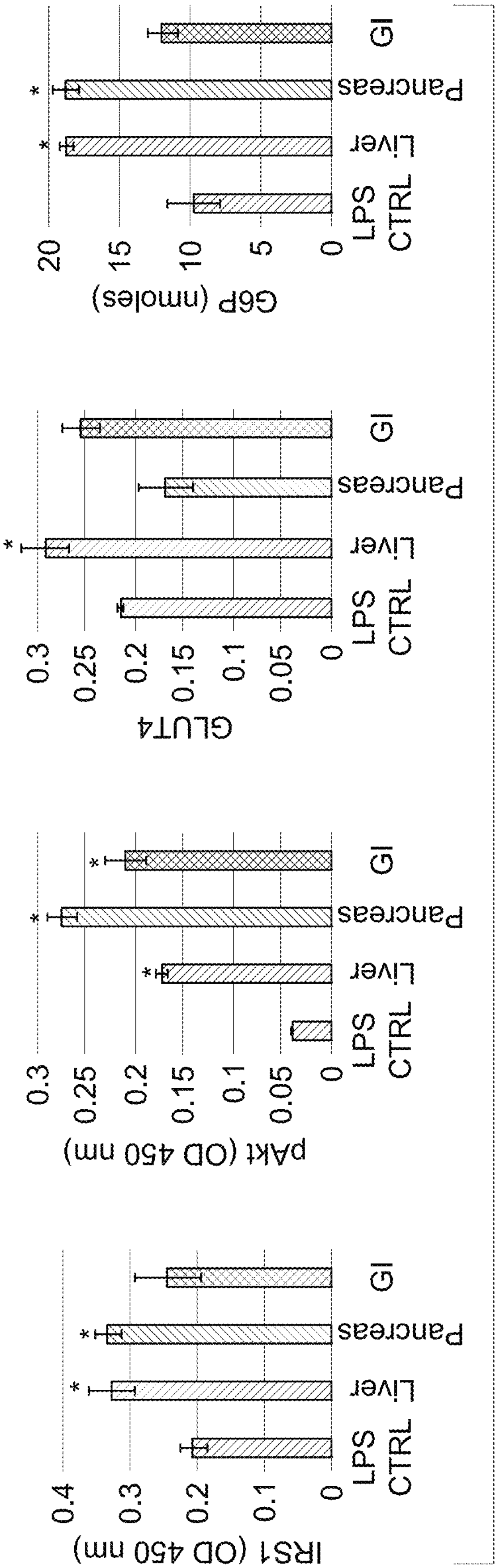
FIG. 10A shows hypothalamic markers of insulin receptor substrate 1 (IRS1), phosphorylated protein kinase B (phos-Akt), glucose transporter type 4 (GLUT4), and glucose-6-phosphate (G-6-phos)
Figure 10B:
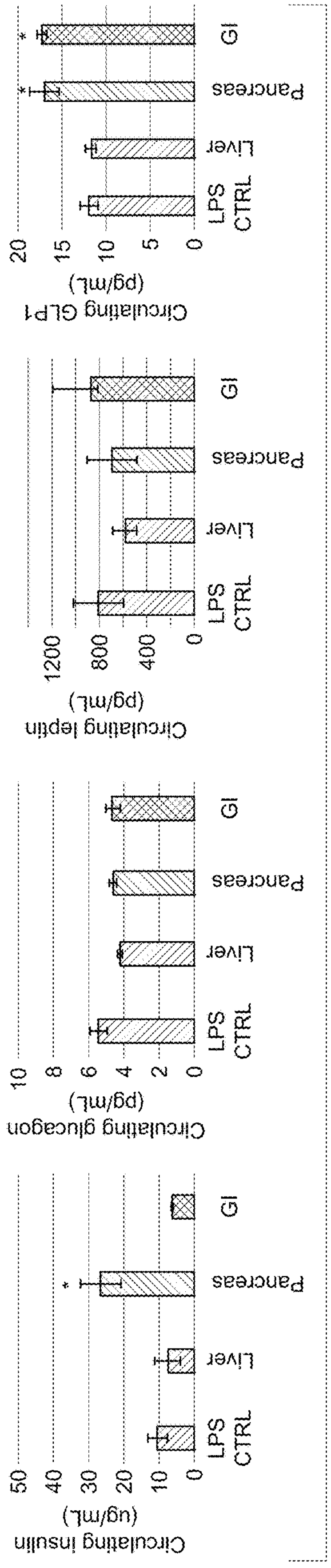
FIG. 10B shows circulating markers of circulating hormones and markers from the collected blood samples, including insulin, glucagon, leptin, and GLP1 concentrations.

FIGS. 10A-B show comparisons of the effects of alternate pFUS stimulation sites on metabolic markers. FIG. 10A shows hypothalamic markers for the animals stimulated using pFUS. Elisa optical intensities or concentrations of molecules associated with insulin signaling and glucose utilization, including insulin receptor substrate 1 (IRS1), phosphorylated protein kinase B (phos-Akt), glucose transporter type 4 (GLUT4), and glucose-6-phosphate (G-6-phos). Data is shown for the LPS-control (no pFUS; LPS CTRL), liver pFUS (liver), pancreatic pFUS (pancreas), and Gastrointestinal Tract pFUS (GI). FIG. 8B shows circulating markers for the animals stimulated using pFUS. Elisa-based concentrations of circulating hormones and markers from the collected blood samples, including insulin, glucagon, leptin, and GLP1 concentrations. The asterisks mark statistical significance using two-sided t-test versus LPS only controls (with p-value thresholds of <0.05). n-6 for each experimental condition.

Gastrointestinal (GI) pFUS had a significantly different effect on hypothalamic and circulating metabolic markers (FIGS. 10A and 10B) compared to the hepatic stimulation results. Like the hepatic stimulus, GI stimulation had no effect on circulating insulin, glucagon, or leptin. However, GI stimulation also had no effect on IRS activity or GLUT4 and glucose-6-phosphate levels within the hypothalamus. Thus, unlike the pancreatic or hepatic stimulation, the GI results suggests that a non-insulin signaling pathway may be responsible for the GI stimulation effect on LPS-induced hyperglycemia. Still, the increased pAkt activity in the GI stimulated hypothalamic samples suggests there may be a hypothalamic involvement in this other pathway, either directly or as an indirect effect. Ultrasound stimulation of the GI may result in the modulation of the incretin glucagon-like peptide 1 (GLP-1) secretion within the small intestine in certain embodiments of the present techniques.

Figure 11A:
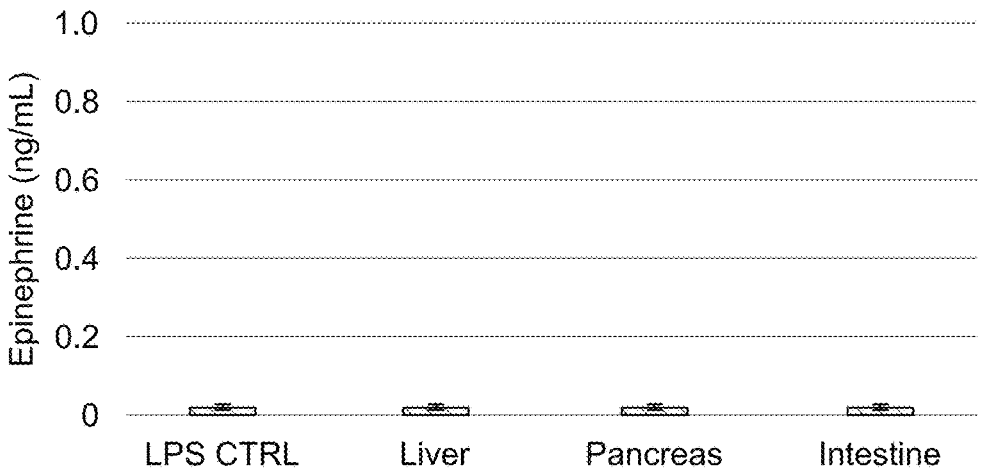
FIG. 11A shows circulating concentrations of epinephrine after pFUS at each target stimulus site and LPS/no pFUS controls (LPS CTRL)
Figure 11B:
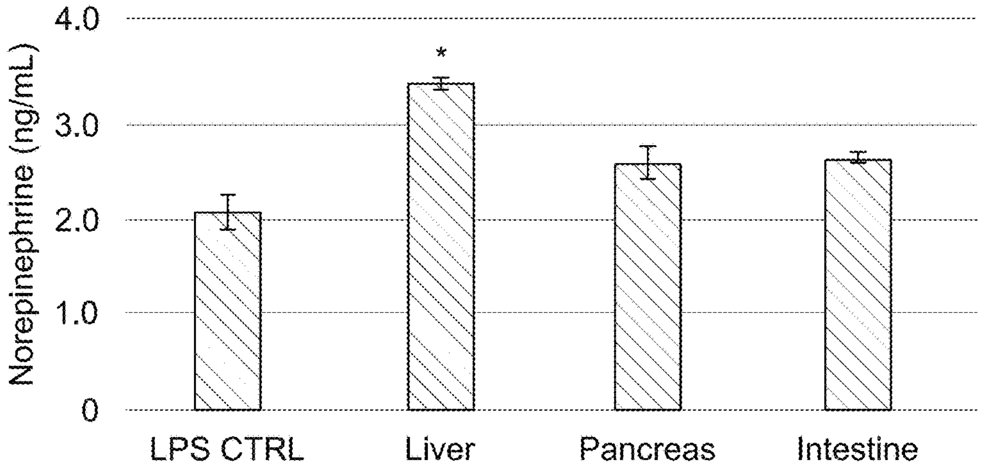
FIG. 11B shows circulating concentrations of norepinephrine after pFUS at each target stimulus site and LPS/no pFUS controls (LPS CTRL)
Figure 11C:
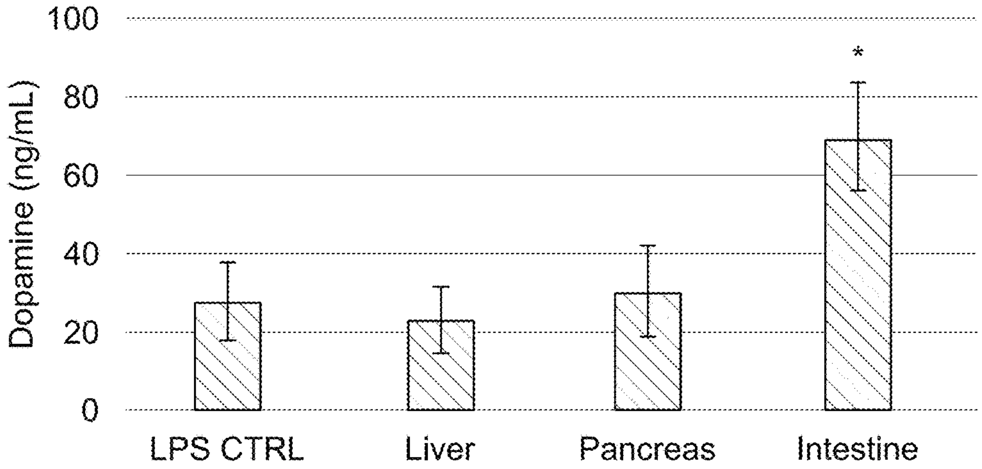
FIG. 11C shows circulating concentrations of dopamine after pFUS at each target stimulus site and LPS/no pFUS controls (LPS CTRL)

FIG. 11A shows circulating concentrations of epinephrine after pFUS at each target stimulus site and LPS/no pFUS controls (LPS CTRL). FIG. 11B shows circulating concentrations of norepinephrine after pFUS at each target stimulus site and LPS/no pFUS controls (LPS CTRL). FIG. 11C shows circulating concentrations of dopamine after pFUS at each target stimulus site and LPS/no pFUS controls (LPS CTRL). The asterisks mark statistical significance using two-sided t-test versus LPS only control (with p-value thresholds of <0.05). N=6 for each experimental condition. As provided herein, liver pFUS resulted in increased in circulating norepinephrine, while pancreatic stimulation resulted in no apparent change in neurotransmitter concentrations and intestinal stimulation resulted in a dopamine specific change in neurotransmitter profile (FIG. 11A-C). Sympathetic nerves are co-located at the porta hepatis with glucose and fatty acid sensing afferents fibers; these nerves may provide a mechanism for hepatic vasoconstriction and modulation of blood pressure. Dopamineric neurons are present in the intestine (but to a lesser extent in the liver or pancreas). These nerves are co-localized with the neuroendocrine cells that produce GLP and serve as an additional regulatory component in metabolic control and homeostasis. The data herein demonstrates that pFUS can be applied to rapidly screen for potential therapeutic stimulation sites (of both neural and neuroendocrine origin), and that local, precision stimulation of specific anatomical targets provides a new technique of modulating and further understanding physiological systems.

The pFUS experiments as disclosed herein for both in vivo and in vitro stimulation were performed as follows. The system used for pFUS stimulation consisted of a 1.1 MHz single element transducer (Sonic Concepts H106), a matching network (Sonic Concepts), an RF power amplifier (ENI 350L) and a function generator (Agilent 333120A). The 70 mm diameter transducer had a spherical face with a 65 mm radius of curvature. The transducer had a 20 mm diameter hole in the center into which an imaging transducer is inserted during transducer alignment and anatomical targeting. The numerically simulated pressure profile had a full width at half maximal (FWHM) amplitude of 1.8 mm laterally and 12 mm in the depth direction. Acoustic coupling to the animal was accomplished using a 6 cm cone filled with degassed water. The function generator was used to produce pulsed sinusoidal waveforms that are amplified by the RF amplifier and sent to the impedance-matching network. Experiments in this manuscript used a pulse repetition period of 0.5 ms (corresponding to a pulse repetition frequency of 2000 Hz), a pulse amplitude of 23 W/cm$^2$ (burst average) and a burst duration of 136 microseconds (corresponding to a duty cycle of 0.27). The voltage-to-pressure calibration of the transducer was performed and reported previously using a needle hydrophone (ONDA HNA-0400).

For in vivo experiments as provided herein, vivid E9 or 11L ultrasound system and probe (GE Healthcare) was used for imaging the anatomical target prior to pFUS neuromodulation. The pFUS transducer was then placed on the target area based on this initial image. A second ultrasound scan was also performed using a smaller imaging probe (3S; GE Healthcare), which is placed in the opening of the pFUS transducer and coupling cone. The imaging beam of the 3S probe was aligned with the pFUS transducer, and enabled confirmation of the organ and anatomical target of interest. Ultrasound stand-offs were utilized as needed to adjust the depth of the pFUS transducer focus. Anatomical markers were used to locate and align the ultrasound stimulus to each target stimulation site: The anatomical markers used to locate the no dose ganglion included the internal carotid artery (as the vagus runs along it towards the skull) and the posterior lacerated foramen where the ganglion is known to exist as a somal swelling of the vagus nerve at the base of the skull. For the sacral ganglia, the four sacral vertebrae were located, and the ultrasound transducer was aligned in the direction of the sacral foramina. The anatomical marker used for the liver stimulation experiments was the porta hepatis (or entry point of the portal vein into the liver). For the pancreas, the splenic vein (imaged via the left lateral side through the spleen as to avoid nonspecific hepatic stimulation) was used as an anatomical marker for the pancreatic tail. The pancreatic tail was selected as it is known to contain dense population of islet cells and is distal from the duodenum. Imaging of the upper left quadrant of the peritoneal cavity was used to identify the jejunum region of the small intestine, which under diagnostic imaging with Doppler ultrasound appears as a highly vascularized folded structure bearing multitude of folds. FIG. 8A and FIG. 9A provide schematic images and descriptions of the locations of the ganglia and end-organ anatomical ultrasound targets.

Adult male Sprague-Dawly rats 8 to 12 weeks old (250-300 g; Charles River Laboratories) were housed on 12-hour light/dark cycles and acclimatized for one week before experiments were conducted. Housing was maintained at 25° C. and water and regular rodent chow were available ad libitum. Lipopolysaccharide (LPS) from *Escherichia coli* (0111: B4; Sigma Aldrich) was used to produce metabolic dysfunction (i.e. hyperglycemia). 10 mg/kg of LPS was administered by intraperitoneal injection, and after LPS administration blood was collected from the tail vein at 0, 5, 15, 30, and 60-minute timepoints. The selected timepoints corresponded to the onset and advancement of hyperinsulemia/hyperglycemia within the LPS-induced cytokine storm and insulin resistance model. Blood glucose concentration were measured by a OneTouch Elite glucometer (LifeScan; Johnson and Johnson). Following the 60 minutes timepoint, brain tissue (hypothalamic) samples were also collected at termination and homogenized in a solution of phosphate-buffered saline (PBS) containing phosphatase (0.2 mM phenylmethylsulfonyl fluoride, 5 ug/mL aprotinin, 1 mM benzamidine, 1 mM sodium orthovandate, and 2 uM cantharidin) and protease inhibitors (1 uL to 20 mg of tissue as per Roche Diagnostic instructions). Additional tissue samples (e.g. ganglia, spleen, liver, and intestinal tissue) were also obtained at 60 minutes and flash frozen in liquid nitrogen for later analysis. Blood samples collected throughout the study were stored with disodium (ethylenedinitrilo) tetraacetic acid (EDTA) anti-coagulant. All sample were stored at −80° C. prior to analysis. Tissue and terminal blood samples were analyzed by enzyme-linked immunosorbent assay (ELISA) for TNF (tumor necrosis factor; Invitrogen), metabolic hormone or signaling molecules: including insulin (Crystal Chem), glucagon (Aviva Systems Biology), leptin (Aviva Systems Biology), IRS1 (insulin receptor substrate 1; Santa Cruz), phos-Akt (phosphorylated protein kinase B; MyBioSource), GLUT4 (glucose transporter type 4; Lifespan Biosciences), and glucose-6-phosphate (G-6-phos; Lifespan Biosciences), according to manufactures instructions. Catecholamines concentrations were measured from tissue samples using a HPLC protocol; briefly, serum samples were injected directly into the machine with no pre-treatment. Tissue homogenates were initially homogenized with 0.1-M perchloric acid and centrifuged for 15 min, after which the supernatant was separated, and the sample injected into the HPLC. Catecholamines norepinephrine and epinephrine were analyzed by HPLC with inline ultraviolet detector. The test column used in this analysis was a Supelco Discovery C18 (15-cm×4.6-mm inside diameter, 5-μm particle size). A biphasic mobile phase comprised of [A] acetonitrile: [B] 50=mM $KH_2PO_4$, set to pH 3 (with phosphoric acid). The solution was then buffered with 100-mg/L EDTA and 200-mg/L 1-octane-sulfonic acid. Final concentration of mobile phase mixture was set to 5:95, A:B. A flow rate of 1 mL/min was used to improve overall peak resolution while the column was held to a consistent 20° C. to minimize pressure compaction of the column resulting from the viscosity of the utilized mobile phase. The UV detector was maintained at a 254-nm wavelength, which is known to capture the absorption for catecholamines including norepinephrine, epinephrine, and dopamine.

For stimulation, animals were anesthetized with 2-4% isoflurane and laid on a water circulating warming pad to prevent hyperthermia during the procedure. Prior to neuromodulation, the area above the anatomical area of interest was shaved with a disposable razor and animal hair clippers. After targeting (as described above), the ultrasound stimulus was applied for a duration of 1 minute. The LPS was then administered immediately following the first ultrasound stimulus (as described above). A second 1-minute ultrasound stimulus was then applied following the LPS administration for a total duration of 2 minutes. The animal was then allowed to incubate under anesthesia, and blood samples were taken as described above. After incubation, the animal was euthanized, and tissue and blood samples were taken as described above.

The disclosed neuromodulation techniques may result in different changes to glucose transporter pathway molecules and/or incretin pathway molecules in different tissues, such as the intestine, GI tract, and kidney. In one embodiment, SGLT2 decreases in the kidney are concurrent with increases in GLP1, SGLT1, GLUT2, and GLUT5 in the intestine. As a result of the complex overall changes, a patient's glycemic index may be lowered as neuromodulation changes in the kidney act to prevent reabsorption of glucose back into the blood and the neuromodulation changes in the intestine act to increase gastric emptying. The changes may be mediated by the hypothalamus through signaling from the liver post-neuromodulation.

In certain embodiments, the neuromodulation as provided herein may be used as a treatment for a subject having a metabolic disorder. Also provided herein are techniques that may be applied to the treatment of glucose metabolism and associated disorders and that may alter disease progression. In one embodiment, liver modulation at one or more regions of interest may be used to treat diabetes (i.e., type 1 or type 2 diabetes), hyperglycemia, sepsis, trauma, infection, diabetes-associated dementia, obesity, or other eating or metabolic disorders. In one embodiment, a patient diagnosed with a disease may present for neuromodulation treatment. After treatment, the patient may have achieved clinical benchmarks that are associated with a healthy patient. For example, a patient with diabetes may present with blood glucose and/or insulin levels outside of a normal range. Post treatment, the patient may have blood glucose and/or insulin levels that are in the normal range. Typical measurements for abnormal insulin and glucose utilization include the fasting glucose exam, the oral glucose tolerance assay, continuous glucose monitoring, the HOMA score or index, glucose and insulin clamp, and other related techniques.

As provided herein, the neuromodulation treatment as provided herein may involve energy application to a region of interest as part of a treatment regimen. The treatment regimen may include one dose or multiple doses applied within a predefined treatment time. For example, the neuromodulation may be once daily at the region of interest (e.g., the porta hepatis), whereby the once daily treatment may be according to preset modulation parameters, for two or more consecutive days.

In certain embodiments, the energy is applied to target tissues that are internal tissues or organs that are difficult to access using electrical stimulation techniques. Contemplated tissue targets include gastrointestinal (GI) tissue (stomach, intestines), muscle tissue (cardiac, smooth and skeletal), epithelial tissue (epidermal, organ/GI lining), connective tissue, glandular tissues (exocrine/endocrine), etc. In one example, focused application of energy at a neuromuscular junction facilitates neurotransmitter release at the neuromuscular junction without an upstream action potential. In other example, focused application of energy at end axon terminals provide a cumulative activity that triggers action potentials within sensory neurons. Still, in other examples, focused application of energy at secretory cells with or without neural near neighbor cells causes activation of those cells and secretion. Contemplated modulation targets may include portions of a pancreas responsible for controlling insulin release, portions of the liver responsible for glucose regulation, or portions of a kidney responsible for glucose reabsorption or excretion.

Neuromodulation to the targeted regions of interest may exert a change in physiological processes to interrupt, decrease, or augment one or more physiological pathways in a subject to yield the desired physiological outcome. Further, because the local energy application may result in systemic changes, different physiological pathways may be changed in different ways and at different locations in the body to cause an overall characteristic profile of physiological change in the subject caused by and characteristic of the targeted neuromodulation for a particular subject. While these changes are complex, the present neuromodulation techniques provide one or more measurable targeted physiological outcomes that, for the treated subjects, are the result of the neuromodulation and that may not be achievable without the application of energy to the targeted region/s of interest or other intervention. Further, while other types of intervention (e.g., drug treatment) may yield a subset of the physiological changes caused by neuromodulation, in certain embodiments, the profile of the induced physiological changes as a result of the neuromodulation may be unique to the neuromodulation (and its associated modulation parameters) at the targeted region/s of interest and may differ from patient to patient.

The neuromodulation techniques discussed herein may be used to cause a physiological outcome of a change in concentration (e.g., increased, decreased) of a molecule of interest and/or a change in characteristics of a molecule of interest, such as a glucose transporter pathway molecule and/or an incretin pathway molecule. As provided herein, glucose transporter pathway molecules are a group of membrane proteins that facilitate the transport of glucose across the plasma membrane. Glucose transporter pathway molecules may include one or more of a GLUT or SLC2A family protein, such as GLUT-1, GLUT-2, GLUT-3, GLUT-4, GLUT-5, GLUT-6, GLUT-7, GLUT-8, GLUT-9, GLUT-10, GLUT-11, GLUT-12, or GLUT-13. As provided herein, incretin pathway molecules may include one or more of glucagon-like peptide-1 (GLP-1) and glucose-dependent insulinotropic polypeptide (GIP), known as incretins, based on their ability to enhance glucose-stimulated insulin secretion. Incretins are secreted by endocrine cells in the small intestine. Other approaches include stimulating tissue and targeting changes in molecules upstream of the incretins and their secretion, including enzymes associated with their production or release, which include DPP-4.

Causing a change via neuromodulation of a molecule of interest, i.e., one or more a glucose transporter pathway molecule and/or an incretin pathway molecule may refer to modulating or influencing a concentration (circulating, tissue) or characteristics (covalent modification) of a molecule as a result of energy application to one or more regions of interest (e.g., a first region of interest, a second region of interest, and so on) in one or more tissues (e.g., a first tissue, a second tissue, and so on). Modulation of a glucose transporter pathway molecule and/or an incretin pathway molecule may include changes in characteristics of the molecule such as expression, secretion, translocation of proteins and direct activity changes based on ion channel effects either derived from the energy application itself or as a result of molecules directly effecting ion channels. Modulation of a molecule of interest may also refer to maintaining a desired concentration of the molecule, such that expected changes or fluctuations in concentration do not occur as a result of the neuromodulation. Modulation of a molecule of interest may refer to causing changes in molecule characteristics, such as enzyme-mediated covalent modification (changes in phosphorylation, aceylation, ribosylation, etc.). That is, it should be understood that selective modulation of a molecule of interest may refer to molecule concentration and/or molecule characteristics. The molecule of interest may be a biological molecule, such as one or more of carbohydrates (monosaccharaides, polysaccharides), lipids, nucleic acids (DNA, RNA), or proteins. In certain embodiments, the molecule of interest may be a signaling molecule such as a hormone (an amine hormone, a peptide hormone, or a steroid hormone).

The disclosed neuromodulation and cellular modulation techniques may be used in conjunction with a neuromodulation system. FIG. 9 is a schematic representation of a system 10 for neuromodulation to achieve neurotransmitter release and/or activate components (e.g., the presynaptic cell, the postsynaptic cell) of a synapse in response to an application of energy. The depicted system includes a pulse generator 14 coupled to an energy application device 12 (e.g., an ultrasound transducer). The energy application device 12 is configured to receive energy pulses, e.g., via leads or wireless connection, that in use are directed to a region of interest of an internal tissue or an organ of a subject, which in turn results in a change in a glucose transporter pathway molecule and/or an incretin pathway molecule. In certain embodiments, the pulse generator 14 and/or the energy application device 12 may be implanted at a biocompatible site (e.g., the abdomen), and the lead or leads couple the energy application device 12 and the pulse generator 14 internally. For example, the energy application device 12 may be a MEMS transducer, such as a capacitive micromachined ultrasound transducer.

In certain embodiments, the energy application device 12 and/or the pulse generator 14 may communicate wirelessly, for example with a controller 16 that may in turn provide instructions to the pulse generator 14. In other embodiments, the pulse generator 14 may be an extracorporeal device, e.g., may operate to apply energy transdermally or in a noninvasive manner from a position outside of a subject's body, and may, in certain embodiments, be integrated within the controller 16. In embodiments in which the pulse generator 14 is extracorporeal, the energy application device 12 may be operated by a caregiver and positioned at a spot on or above a subject's skin such that the energy pulses are delivered transdermally to a desired internal tissue. Once positioned to apply energy pulses to the desired site, the system 10 may initiate neuromodulation to achieve clinical effects such as treatment of a metabolic disorder.

In certain embodiments, the system 10 may include an assessment device 20 that is coupled to the controller 16 and assesses characteristics that are indicative of whether the changes in a glucose transporter pathway molecule and/or an incretin pathway molecule as a result of the neuromodulation have been achieved. In one embodiment, the characteristics may be local. For example, the modulation may result in local tissue or function changes, such as tissue structure changes, local change of concentration of certain molecules, tissue displacement, increased fluid movement, etc.

The modulation may result in systemic or non-local changes, and the targeted physiological outcome may be related to a change in concentration of circulating molecules or a change in a characteristic of a tissue that does not include the region of interest to which energy was directly applied. In one example, the displacement may be a proxy measurement for a desired modulation, and displacement measurements below an expected displacement value may result in modification of modulation parameters until an expected displacement value is induced. Accordingly, the assessment device 20 may be configured to assess concentration changes in some embodiments. In some embodiments, the assessment device 20 may be an imaging device configured to assess changes in organ size and/or position. While the depicted elements of the system 10 are shown separately, it should be understood that some or all of the elements may be combined with one another. Further, some or all of the elements may communicate in a wired or wireless manner with one another.

Based on the assessment, the modulation parameters of the controller 16 may be altered. For example, if a desired modulation is associated with a change in concentration (circulating concentration or tissue concentration of one or more molecules) within a defined time window (e.g., 5 minutes, 30 minutes after a procedure of energy application starts) or relative to a baseline measurements at the start or before initiation of a procedure, a change of the modulation parameters such as pulse frequency or other parameters may be desired, which in turn may be provided to the controller 16, either by an operator or via an automatic feedback loop, for defining or adjusting the energy application parameters or modulation parameters of the pulse generator 14.

The system 10 as provided herein may provide energy pulses according to various modulation parameters. For example, the modulation parameters may include various stimulation time patterns, ranging from continuous to intermittent. With intermittent stimulation, energy is delivered for a period of time at a certain frequency during a signal-on time. The signal-on time is followed by a period of time with no energy delivery, referred to as signal-off time. The modulation parameters may also include frequency and duration of a stimulation application. The application frequency may be continuous or delivered at various time periods, for example, within a day or week. The treatment duration may last for various time periods, including, but not limited to, from a few minutes to several hours. In certain embodiments, treatment duration with a specified stimulation pattern may last for one hour, repeated at, e.g., 72 hour intervals. In certain embodiments, treatment may be delivered at a higher frequency, say every three hours, for shorter durations, for example, 30 minutes. The application of energy, in accordance with modulation parameters, such as the treatment duration and frequency, may be adjustably controlled to achieve a desired result.

FIG. 10 is a block diagram of certain components of the system 10. As provided herein, the system 10 for neuromodulation may include a pulse generator 14 that is adapted to generate a plurality of energy pulses for application to a tissue of a subject. The pulse generator 14 may be separate or may be integrated into an external device, such as a controller 16. The controller 16 includes a processor 30 for controlling the device. Software code or instructions are stored in memory 32 of the controller 16 for execution by the processor 30 to control the various components of the device. The controller 16 and/or the pulse generator 14 may be connected to the energy application device 12 via one or more leads 33 or wirelessly The controller 16 also includes a user interface with input/output circuitry 34 and a display 36 that are adapted to allow a clinician to provide selection inputs or modulation parameters to modulation programs. Each modulation program may include one or more sets of modulation parameters including pulse amplitude, pulse width, pulse frequency, etc. The pulse generator 14 modifies its internal parameters in response to the control signals from controller device 16 to vary the stimulation characteristics of energy pulses transmitted through lead 33 to an subject to which the energy application device 12 is applied. Any suitable type of pulse generating circuitry may be employed, including but not limited to, constant current, constant voltage, multiple-independent current or voltage sources, etc. The energy applied is a function of the current amplitude and pulse width duration. The controller 16 permits adjustably controlling the energy by changing the modulation parameters and/or initiating energy application at certain times or cancelling/suppressing energy application at certain times. In one embodiment, the adjustable control of the energy application device is based on information about a concentration of one or more molecules in the subject (e.g., a circulating molecule). If the information is from the assessment device 20, a feedback loop may drive the adjustable control. For example, if a circulating glucose concentration in blood or urine, as measured by the assessment device 20, is above a predetermined threshold or range, the controller 16 may initiate energy application to a region of interest (e.g., liver) and with modulation parameters that are associated with a reduction in circulating glucose. The initiation of energy application may be triggered by the glucose concentration drifting above a predetermined (e.g., desired) threshold or outside a predefined range. In another embodiment, the adjustable control may be in the form of altering modulation parameters when an initial application of energy does not result in an expected change in a targeted physiological outcome (e.g., concentration of a molecule of interest) within a predefined time frame (e.g., 1 hour, 2 hours, 4 hours, 1 day).

In one embodiment, the memory 32 stores different operating modes that are selectable by the operator. For example, the stored operating modes may include instructions for executing a set of modulation parameters associated with a particular treatment site, such as regions of interest in the liver, pancreas, gastrointestinal tract, spleen. Different sites may have different associated modulation parameters. Rather than having the operator manually input the modes, the controller 16 may be configured to execute the appropriate instruction based on the selection. In another embodiment, the memory 32 stores operating modes for different types of treatment. For example, activation may be associated with a different stimulating pressure or frequency range relative to those associated with depressing or blocking tissue function. In a specific example, when the energy application device is an ultrasound transducer, the time-averaged power (temporal average intensity) and peak positive pressure are in the range of 1 $mW/cm^2$-30,000 $mW/cm^2$ (temporal average intensity) and 0.1 MPa to 7 MPa (peak pressure). In one example, the temporal average intensity is less than 35 $W/cm^2$ in the region of interest to avoid levels associated with thermal damage & ablation/cavitation. In another specific example, when the energy application device is a mechanical actuator, the amplitude of vibration is in the range of 0.1 to 10 mm. The selected frequencies may depend on the mode of energy application, e.g., ultrasound or mechanical actuator.

In another embodiment, the memory 32 stores a calibration or setting mode that permits adjustment or modification of the modulation parameters to achieve a desired result. In one example, the stimulation starts at a lower energy parameter and increases incrementally, either automatically or upon receipt of an operator input. In this manner, the operator may achieve tuning of the induced effects as the modulation parameters are being changed.

The system may also include an imaging device that facilitates focusing the energy application device 12. In one embodiment, the imaging device may be integrated with or the same device as the energy application device 12 such that different ultrasound parameters (frequency, aperture, or energy) are applied for selecting (e.g., spatially selecting) a region of interest and for focusing energy to the selected region of interest for targeting and subsequently neuromodulation. In another embodiment, the memory 32 stores one or more targeting or focusing modes that is used to spatially select the region of interest within an organ or tissue structure. Spatial selection may include selecting a subregion of an organ to identify a volume of the organ that corresponds to a region of interest. Spatial selection may rely on image data as provided herein. Based on the spatial selection, the energy application device 12 may be focused on the selected volume corresponding to the region of interest. For example, the energy application device 12 may be configured to first operate in the targeting mode to apply a targeting mode energy that is used to capture image data to be used for identifying the region of interest. The targeting mode energy is not at levels and/or applied with modulation parameters suitable for preferential activation. However, once the region of interest is identified, the controller 16 may then operate in a treatment mode according to the modulation parameters associated with preferential activation.

The controller 16 may also be configured to receive inputs related to the targeted physiological outcomes as an input to the selection of the modulation parameters. For example, when an imaging modality is used to assess a tissue characteristic, the controller 16 may be configured to receive a calculated index or parameter of the characteristic. Based on whether the index or parameter is above or below a predefined threshold, the modulation parameters may be modified. In one embodiment, the parameter can be a measure of tissue displacement of the affected tissue or a measure of depth of the affected tissue. Other parameters may include assessing a concentration of one or more molecules of interest (e.g., assessing one or more of a change in concentration relative to a threshold or a baseline/control, a rate of change, determining whether concentration is within a desired range). Further, the energy application device 12 (e.g., an ultrasound transducer) may operate under control of the controller 16 to a) acquire image data of a tissue that may be used to spatially select a region of interest within the target tissue b) apply the modulating energy to the region of interest and c) acquire an image to determine that the targeted physiological outcome associated with a change in a glucose transporter pathway molecule and/or an incretin pathway molecule has occurred (e.g., via displacement measurement). In such an embodiment, the imaging device, the assessment device 20 and the energy application device 12 may be the same device.

In another implementation, a desired modulation parameter set may also be stored by the controller 16. In this manner, subject-specific parameters may be determined. Further, the effectiveness of such parameters may be assessed over time. If a particular set of parameters is less effective over time, the subject may be developing insensitivity to activated pathways. If the system 10 includes an assessment device 20, the assessment device 20 may provide feedback to the controller 16. In certain embodiments, the feedback may be received from a user or an assessment device 20 indicative of a characteristic of the target physiological outcome. The controller 16 may be configured to cause the energy application device to apply the energy according to modulation parameters and to dynamically adjust the modulation parameters based on the feedback. For example, based on the feedback, the processor 16 may automatically alter the modulation parameters (e.g., the frequency, amplitude, or pulse width of an ultrasound beam or mechanical vibration) in real time and responsive to feedback from the assessment device 20.

In one example, the present techniques may be used to treat a subject with a metabolic disorder. The present techniques may be used to regulate blood glucose level in subjects with disorders of glucose regulation. Accordingly, the present techniques may be used to promote homeostasis of a molecule of interest or to promote a desired circulating concentration or concentration range of one or more molecules of interest (e.g., glucose, insulin, glucagon, or a combination thereof). In one embodiment, the present techniques may be used to control circulating (i.e., blood) glucose levels. In one embodiment, the following thresholds may be used to maintain blood glucose levels in a dynamic equilibrium in the normal range:

Fasted:
- Less than 50 mg/dL (2.8 mmol/L): Insulin Shock
- 50-70 mg/dL (2.8-3.9 mmol/L): low blood sugar/hypoglycemia
- 70-110 mg/dL (3.9-6.1 mmol/L): normal
- 110-125 mg/dL (6.1-6.9 mmol/L): elevated/impaired (pre-diabetic)
- 125 (7 mmol/L): diabetic Non-Fasted (Postprandial Approximately 2 Hours After Meal):
- 70-140 mg/dL: Normal
- 140-199 mg/dL (8-11 mmol/L): Elevated or "borderline"/prediabetes
- More than 200 mg/dL: (11 mmol/L): Diabetes For example, the techniques may be used to maintain circulating glucose concentration to be under about 200 mg/dL and/or over about 70 mg/dL. The techniques may be used to maintain glucose in a range between about 4-8 mmol/L or about 70-150 mg/dL. The techniques may be used to maintain a normal blood glucose range for the subject (e.g., a patient), where the normal blood glucose range may be an individualized range based on the patient's individual factors such as weight, body mass index, age, gender, genetics, clinical history. Accordingly, the application of energy (e.g., ultrasound energy) to one or more regions of interest may be adjusted in real time based on the desired end concentration of the molecule of interest and may be adjusted in a feedback loop based on input from an assessment device 20. For example, if the assessment device 20 is a glucose monitor (e.g., blood glucose, excreted glucose), the real-time glucose measurements may be used as input to the controller 16.

In another embodiment, the present techniques may be used to induce a characteristic profile of physiological changes. For example, the characteristic profile may include a group of molecules of interest that increase in concentration in the tissue and/or blood as a result of the energy application and another group of molecules of interest that decrease in concentration in the tissue and/or blood as a result of the energy application. The characteristic profile may include a group of molecules that do not change as a result of the energy application. The characteristic profile may define concurrent changes that are associated with a desired physiological outcome. For example, the profile may include a decrease in circulating glucose seen together with an increase in excreted glucose in the urine.

The desired target tissue may be an internal tissue or an organ that includes synapses of axon terminals of peripheral nerves and non-neuronal cells. The synapses may be stimulated by direct application of energy to the axon terminals within a field of focus of the ultrasound transducer focused on a region of interest of the target tissue or organ to cause release of molecules into the synaptic space. For example, the release of neurotransmitters and/or the change in ion channel activity in turn causes downstream effects such as activation of glucose metabolism. The region of interest may be selected to include a certain type of axon terminal, such as an axon terminal of a particular neuron type and/or one that forms a synapse with a certain type of non-neuronal cell. Accordingly, the region of interest may be selected to correspond to a portion of the target tissue with the desired axon terminals (and associated non-neuronal cells). The energy application may be selected to preferentially trigger a release of one or more molecules such as neurotransmitters from the nerve within the synapse or directly activate the non-neuronal cell itself through direct energy transduction (i.e. mechanotransduction or voltage-activated proteins within the non-neuronal cells), or cause an activation within both the neural and non-neuronal cells that elicits a desired physiological effect. The region of interest may be selected as the site of nerve entry into the organ. In one embodiment, liver stimulation or modulation may refer to a modulation of the region of interest at or adjacent to the porta hepatis.

The energy may be focused or substantially concentrated on a region of interest and to only part of (i.e., a subregion of) the internal tissue or internal organ, e.g., less than about 50%, 25%, 10%, or 5% of the total volume of the tissue or organ. In one embodiment, energy may be applied to two or more regions of interest in the target tissue, and the total volume of the two or more regions of interest may be less than about 90%, 50%, 25%, 10%, or 5% of the total volume of the tissue. In one embodiment, the energy is applied to only about 1%-50% of the total volume of the tissue, to only about 1%-25% of the total volume of the tissue, to only about 1%-10% of the total volume of the tissue, or to only about 1%-5% of the total volume of the tissue. In certain embodiments, only axon terminals 46 in the region of interest of the target tissue would directly receive the applied energy and release neurotransmitters while the unstimulated axon terminals outside of the region of interest do not receive substantial energy and, therefore, are not activated/stimulated in the same manner. In some embodiments, axon terminals 46 in the portions of the tissue directly receiving the energy would induce an altered neurotransmitter release. In this manner, tissue subregions may be targeted for neuromodulation in a granular manner, e.g., one or more subregions may be selected. In some embodiments, the energy application parameters may be chosen to induce preferential activation of either neural or non-neuronal components within the tissue directly receiving energy to induce a desired combined physiological effect. In certain embodiments, the energy may be focused or concentrated within a volume of less than about 25 $mm^3$. In certain embodiments, the energy may be focused or concentrated within a volume of about 0.5 $mm^3$-50 $mm^3$. A focal volume and a focal depth for focusing or concentrating the energy within the region of interest may be influenced by the size/configuration of the energy application device 12. The focal volume of the energy application may be defined by the field of focus of the energy application device 12.

As provided herein, the energy may be substantially applied only to the region or regions of interest to preferentially activate the synapse in a targeted manner to achieve targeted physiological outcomes and is not substantially applied in a general or a nonspecific manner across the entire tissue. Accordingly, only a subset of a plurality of different types of axon terminals in the tissue is exposed to the direct energy application. Imaging data of the tissue or organ may serve to identify the region of interest of the targeted organ such that the energy may be focused on the region of interest and not the surrounding tissue. For example, the regions of interest within organs containing either blood vessels, nerves, or other anatomical landmarks may be spatially selected and used to identify areas with specific axon terminals and synapses. The disclosed selection of the region of interest using imaging information may be used in conjunction with organs or tissue structures (e.g., liver, pancreas, gastrointestinal tissue).

The disclosed techniques may be used in assessment of neuromodulation or cellular modulation effects, which in turn may be used as an input or a feedback for selecting or modifying neuromodulation parameters. The disclosed techniques may use direct assessments of tissue condition or function as the targeted physiological outcomes. The assessment may occur before (i.e., baseline assessment), during, and/or after the neuromodulation.

The assessment techniques may include at least one of functional magnetic resonance imaging, diffusion tensor magnetic resonance imaging, positive emission tomography, or acoustic monitoring, thermal monitoring. The assessment techniques may also include protein and/or marker concentration assessment. The images from the assessment techniques may be received by the system for automatic or manual assessment. Based on the image data, the modulation parameters may also be modified. For example, a change in organ size or displacement may be utilized as a marker of local neurotransmitter concentration, and used as a surrogate marker for exposure of local cells to phenotype modulating neurotransmitters, and effectively as a marker of predicted effect on glucose metabolic pathways. The local concentration may refer to a concentration within a field of focus of the energy application.

Additionally or alternatively, the system may assess the presence or concentration of one or more molecules in the tissue or circulating in the blood. The concentration in the tissue may be referred to as a local concentration or resident concentration. Tissue may be acquired by a fine needle aspirate, and the assessment of the presence or levels of molecules of interest (e.g., metabolic molecules, markers of metabolic pathways, peptide transmitters, catecholamines) may be performed by any suitable technique known to one of ordinary skilled in the art, e.g., enzyme-linked immunoassays, mRNA sequencing.

In other embodiments, the targeted physiological outcomes may include, but are not limited to, tissue displacement, tissue size changes, a change in concentration of one or more molecules (either local, non-local, or circulating concentration), a change in gene or marker expression, afferent activity, and cell migration, etc. For example, tissue displacement (e.g., liver displacement) may occur as a result of energy application to the tissue. By assessing the tissue displacement (e.g., via imaging), other effects may be estimated. For example, a certain displacement may be characteristic of a particular change in molecule concentration. In one example, a 5% liver displacement may be indicative of or associated with a desired reduction in circulating glucose concentration based on empirical data. In another example, the tissue displacement may be assessed by comparing reference image data (tissue image before application of energy to the tissue) to post-treatment image data (tissue image taken after application of energy to the tissue) to determine a parameter of displacement. The parameter may be a maximum or average displacement value of the tissue. If the parameter of displacement is greater than a threshold displacement, the application of energy may be assessed as being likely to have caused the desired targeted physiological outcome.

FIG. 11 is a flow diagram of a method 50 for treating a patient (i.e., treatment subject). In the method 50, the subject is identified 52. The subject may be a patient having a metabolic disorder as provided herein, and the identification may be via suitable diagnostic techniques. Once identified, the subject is treated for the metabolic disorder via application of energy to a target tissue of the subject 54. In one embodiment, an energy application device (ultrasound energy, mechanical energy) is positioned such that the energy pulses are focused at a desired region of interest of the internal tissue (e.g., liver, GI, kidney, pancreas) at step 54, and the pulse generator applies one or more energy pulses to the region of interest of the target tissue to preferentially activate a subset of synapses in the target tissue, e.g., to stimulate the axon terminal to change a glucose transporter pathway molecule and/or an incretin pathway molecule as provided herein. In certain embodiments, the method 50 may include a step of assessing the effect of the energy application. For example, one or more direct or indirect assessments may be used. Based on the assessment, the modulation parameters of the one or more energy pulses may be modified (e.g., dynamically or adjustably controlled) to achieve the treatment of the subject.

In one embodiment, assessments may be performed before and after applying energy pulses to assess a change in glucose concentration as a result of the modulation. If the glucose concentration is above or below a threshold, appropriate modification in the modulation parameters may be made. For example, if the glucose concentration with desired physiological outcome, the energy applied during neuromodulation may be stepped back to a minimum level that supports the desired outcome. If the change in the characteristic relative to the threshold is associated with insufficient change in glucose concentration, certain modulation parameters, including, but not limited to, the modulation amplitude or frequency, the pulse shape, the stimulation pattern, and/or the stimulation location may be changed.

Figure 12:
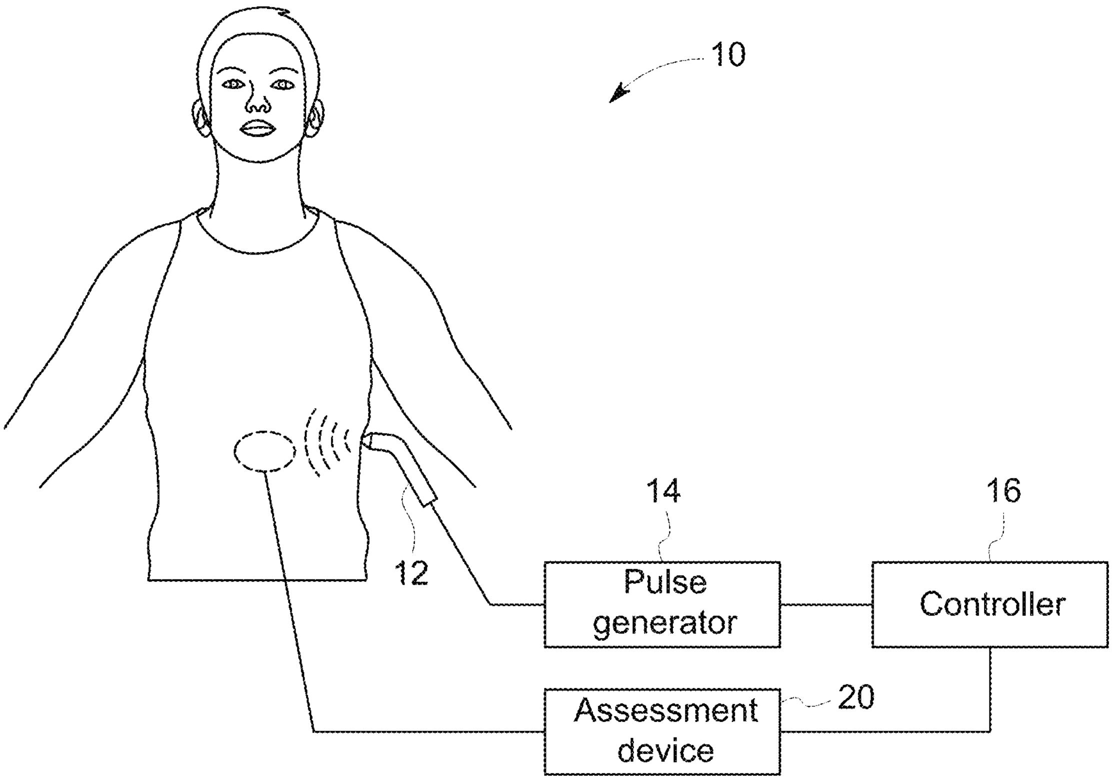
FIG. 12 is a schematic representation of a neuromodulation system using a pulse generator according to embodiments of the disclosure.
Figure 13:
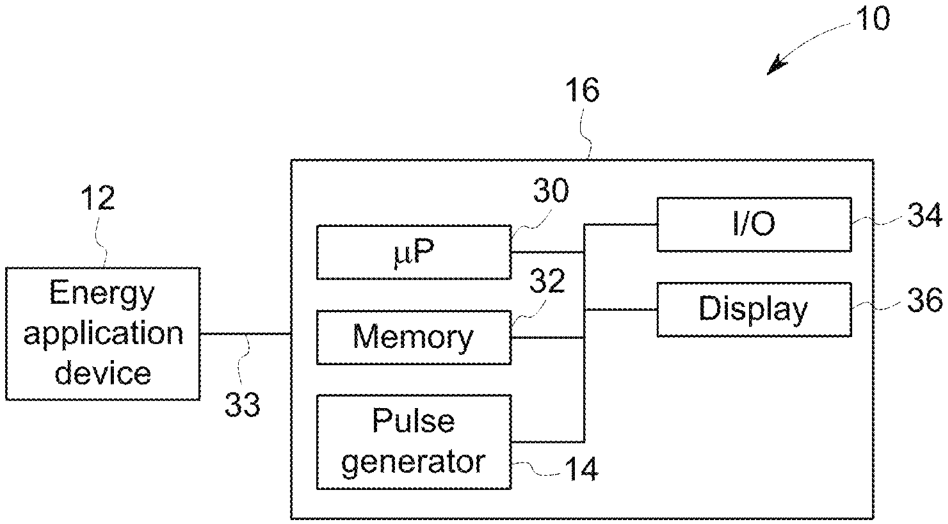
FIG. 13 is a block diagram of a neuromodulation system according to embodiments of the disclosure.
Figure 14:
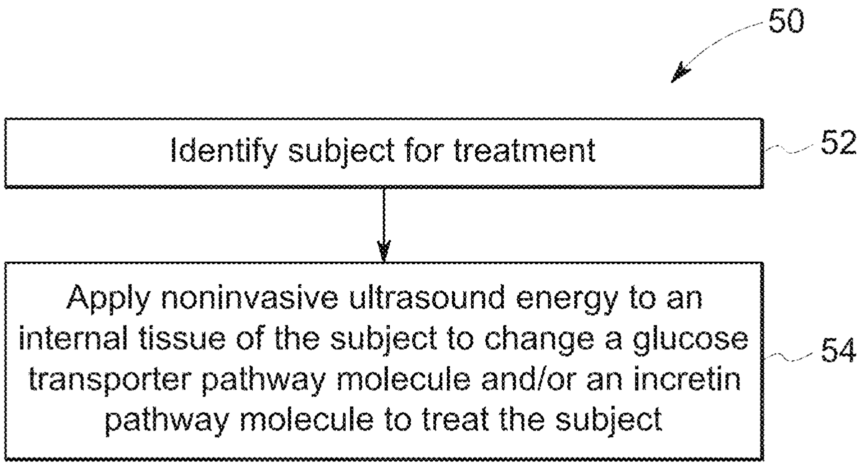
FIG. 14 is a flow diagram of a neuromodulation technique according to embodiments of the disclosure.
Figure 15:
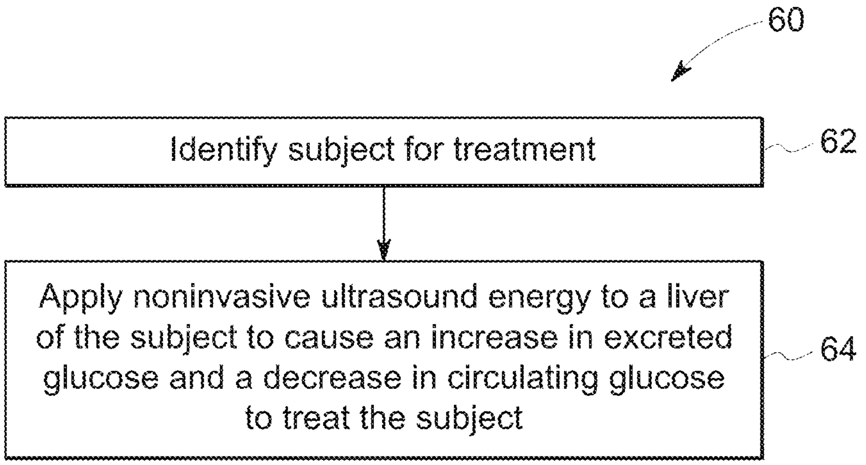
FIG. 15 is a flow diagram of a neuromodulation technique according to embodiments of the disclosure.

FIG. 12 is a flow diagram of a method 60 in which, once identified (block 62), the subject is treated via application of noninvasive ultrasound energy to a region of interest in the liver (block 64). The application of noninvasive ultrasound energy changes glucose transporter pathway molecules and/ or an incretin pathway molecules in one or more tissues in the body as a result of the hepatic neuromodulation. In turn, these changes may cause changes in circulating glucose (e.g., a decrease) and changes in excreted glucose in the urine (e.g., an increase) that are indicative of a successful treatment or a targeted physiological outcome. It should be understood that the neuromodulation may cause a number of physiological effects that are linked to changes glucose transporter pathway molecules and/or an incretin pathway molecules, and that one or more of these changes may be assessed.

The assessed characteristic or condition may be a value or an index, for example, a flow rate, a concentration, a cell population, or any combination thereof, which in turn may be analyzed by a suitable technique. For example, a relative change exceeding a threshold may be used to determine if the modulation parameters are modified. The desired modulation may be assessed via a measured clinical outcome, such as a presence or absence of an increase in tissue structure size (e.g., lymph node size) or a change in concentration of one or more released molecules (e.g., relative to the baseline concentration before the neuromodulation). In one embodiment, a desired modulation may involve an increase in concentration above a threshold, e.g., above a about 50%, 100%, 200%, 400%, 1000% increase in concentration relative to baseline. For blocking treatments, the assessment may involve tracking a decrease in concentration of a molecule over time, e.g., at least a 10%, 20%, 30%, 50%, or 75% decrease in the molecule of interest. Further, for certain subjects, the desired blocking treatment may involve keeping a relatively steady concentration of a particular molecule in the context of other clinical events that may tend to increase the concentration of the molecule. That is, desired blocking may block a potential increase. The increase or decrease or other induced and measurable effect may be measured within a certain time window from the start of a treatment, e.g., within about 5 minutes, within about 30 minutes. In certain embodiments, if the neuromodulation is determined to be desired, the change in the neuromodulation is an instruction to stop applying energy pulses. In another embodiment, one or more parameters of the neuromodulation are changed if the neuromodulation is not desired. For example, the change in modulation parameters may be an increase in pulse repetition frequency, such as a stepwise increase in frequency of 1-10000 Hz and assessment of the desired characteristic until a desired neuromodulation is achieved. In another implementation, a pulse width may be changed. In other embodiments, two or more of the parameters may be changed together, in parallel or in series. If the neuromodulation is not desired after multiple parameter changes, the focus (i.e., the site) of energy application may be changed.

Technical effects of the invention include inducing targeted changes in metabolic pathways and/or molecules via neuromodulation to treat a subject.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for treating a subject having a metabolic disorder, comprising:

applying ultrasound energy to only a subregion of a liver, wherein the subregion comprises a porta hepatis of the liver and stimulating sensory neurons within an internal tissue of the subject to cause a change to a glucose transporter pathway molecule and/or an incretin pathway molecule in the subject to treat the metabolic disorder, wherein the ultrasound energy is applied by an extracorporeal energy application device, and wherein the change of the glucose transporter pathway molecule and/or incretin pathway molecule is at an internal organ that is distal from the internal tissue.

2. The method of claim 1, wherein the glucose transporter pathway molecule comprises GLUT2, GLUT4, SGLT1, SGLT2, or a combination thereof.

3. The method of claim 1, wherein the internal tissue comprises secretory cell compartments or one or more nerve pathways.

4. The method of claim 1, wherein application of the ultrasound energy decreases the subject's glycemic index.

5. A method for treating a subject having a metabolic disorder, comprising:

selecting a region of interest comprising only a subregion of a liver of the subject, wherein the region of interest comprises a porta hepatis of the liver; and applying ultrasound energy to the region of interest of the liver to cause a change to a glucose transporter pathway molecule and/or an incretin pathway molecule in the subject to treat the metabolic disorder, and wherein the change of the glucose transporter pathway molecule and/or incretin pathway molecule is in an internal organ that is distal from the liver in the subject.

6. The method of claim 5, wherein the applied ultrasound energy increases expression of the glucose transporter pathway molecule and/or the incretin pathway molecule in the subject at the internal organ that is distal from the liver in the subject.

7. The method of claim 5, wherein the internal organ comprises secretory cell compartments or one or more nerve pathways.

8. The method of claim 5, wherein the glucose transporter pathway molecule comprises GLUT2.

9. The method of claim 5, wherein the incretin pathway molecule comprises GLP-1.

10. The method of claim 5, wherein the ultrasound energy is applied non-invasively.

11. A method for treating a subject having a metabolic disorder, comprising:

selecting a region of interest in a tissue of the subject, wherein the region of interest is only a subregion of a liver, the subregion comprising a porta hepatis of the liver; and applying ultrasound energy to the region of interest in the tissue to cause a change to a glucose transporter pathway molecule and/or an incretin pathway molecule in the subject to treat the metabolic disorder, and wherein the change of the glucose transporter pathway molecule and/or incretin pathway molecule is in an internal organ that is distal from the tissue in the subject.

12. The method of claim 11, wherein the internal organ comprises a hypothalamus.

13. The method of claim 12, wherein the internal organ comprises secretory cell compartments or one or more nerve pathways.

14. The method of claim 11, wherein the glucose transporter pathway molecule and/or the incretin pathway molecule comprises GLP-1.

* * * * *